(12) United States Patent
Cordoba et al.

(10) Patent No.: US 10,647,007 B2
(45) Date of Patent: May 12, 2020

(54) CAPACITOR SENSOR INCLUDING TWO PLATES HAVING BOTH CONDUCTIVE AND NON CONDUCTIVE REGIONS

(71) Applicant: Verb Surgical Inc., Mountain View, CA (US)

(72) Inventors: Jose Luis Cordoba, Malaga (ES); Pablo E. Garcia Kilroy, Menlo Park, CA (US); Xin Liu, Milpitas, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 101 days.

(21) Appl. No.: 15/706,585

(22) Filed: Sep. 15, 2017

(65) Prior Publication Data

US 2018/0080841 A1    Mar. 22, 2018

Related U.S. Application Data

(60) Provisional application No. 62/395,704, filed on Sep. 16, 2016.

(51) Int. Cl.
*A61B 34/30* (2016.01)
*B25J 13/02* (2006.01)
(Continued)

(52) U.S. Cl.
CPC ........... *B25J 18/04* (2013.01); *A61B 1/00149* (2013.01); *A61B 34/30* (2016.02); *A61B 34/35* (2016.02);
(Continued)

(58) Field of Classification Search
CPC .. G01G 3/12; G01G 7/06; G01G 3/14; G01G 19/414; G01G 21/23; G01G 19/42;
(Continued)

(56) References Cited

U.S. PATENT DOCUMENTS 2,212,823 A    8/1940  Bulk
4,568,371 A    2/1986  Nebelung et al.
(Continued)

FOREIGN PATENT DOCUMENTS

WO    2015/132549 A1    9/2015
WO    2018/053349 A1    3/2018
(Continued)

OTHER PUBLICATIONS

Written Opinion of the International Search Authority dated Jan. 23, 2018 for WO Application No. PCT/US17/051921.
(Continued)

*Primary Examiner* — Brandi N Hopkins
(74) *Attorney, Agent, or Firm* — Womble Bond Dickinson (US) LLP

(57) ABSTRACT

A capacitive sensor for characterizing force or torque includes a first plurality of non-patterned conductive regions and a first plurality of patterned conductive regions, and a second plurality of non-patterned conductive regions and a second plurality of patterned conductive regions. The first and second pluralities of non-patterned conductive regions are facing each other and the first and second pluralities of patterned conductive regions are facing each other.

18 Claims, 24 Drawing Sheets

(51) Int. Cl.
| | |
|---|---|
| *B25J 13/08* | (2006.01) |
| *B25J 18/04* | (2006.01) |
| *G16H 20/40* | (2018.01) |
| *G16H 40/63* | (2018.01) |
| *A61B 34/00* | (2016.01) |
| *B25J 9/10* | (2006.01) |
| *B25J 15/00* | (2006.01) |
| *B25J 17/02* | (2006.01) |
| *A61B 34/37* | (2016.01) |
| *A61B 1/00* | (2006.01) |
| *A61B 34/35* | (2016.01) |
| *G01L 1/14* | (2006.01) |
| *G01L 3/14* | (2006.01) |
| *G01L 5/22* | (2006.01) |
| *A61B 1/313* | (2006.01) |
| *G06F 19/00* | (2018.01) |

(52) U.S. Cl.
CPC .............. *A61B 34/37* (2016.02); *A61B 34/70* (2016.02); *A61B 34/71* (2016.02); *A61B 34/77* (2016.02); *B25J 9/10* (2013.01); *B25J 9/1045* (2013.01); *B25J 13/02* (2013.01); *B25J 15/0019* (2013.01); *B25J 17/0283* (2013.01); *G01L 1/14* (2013.01); *G01L 3/14* (2013.01); *G01L 5/226* (2013.01); *G16H 20/40* (2018.01); *G16H 40/63* (2018.01); *A61B 1/3132* (2013.01); *A61B 2034/715* (2016.02); *B25J 13/085* (2013.01); *G06F 19/3418* (2013.01)

(58) Field of Classification Search
CPC ...... G01G 21/28; G06Q 10/087; G06Q 50/24; G06Q 50/22; G01D 5/24; A61B 5/4585; A61B 5/1036; A61B 5/412; A61B 17/025; A61B 5/4509; A61B 2090/064; A61B 5/6878; A61B 2017/00221; A61B 5/686; A61B 5/1076; A61B 5/4528; A61B 2017/0268; A61B 5/076; A61B 2562/0247; G01L 1/255; G01L 1/165; A61F 2/389; A61F 2/4684; A61F 2/4657; A61F 2002/4666

See application file for complete search history.

(56) References Cited

U.S. PATENT DOCUMENTS

| | | | |
|---|---|---|---|
| 5,150,759 A * | 9/1992 | Borchard | G01G 3/12 177/210 C |
| 5,447,076 A * | 9/1995 | Ziegler | G01L 1/142 73/862.625 |
| 5,797,900 A | 8/1998 | Madhani et al. | |
| 6,360,612 B1 * | 3/2002 | Trantzas | G01L 1/20 73/753 |
| 6,966,428 B1 | 11/2005 | Flynn | |
| 2003/0083648 A1 | 5/2003 | Wang et al. | |
| 2006/0167440 A1 | 7/2006 | Cooper et al. | |
| 2007/0261894 A1 * | 11/2007 | Harish | G01G 7/06 177/211 |
| 2007/0299427 A1 | 12/2007 | Yeung et al. | |
| 2008/0087871 A1 | 4/2008 | Schena | |
| 2008/0190210 A1 * | 8/2008 | Harish | G01L 1/142 73/780 |
| 2009/0114041 A1 * | 5/2009 | Harish | G06Q 10/087 73/862.626 |
| 2013/0023794 A1 | 1/2013 | Stein et al. | |
| 2013/0325033 A1 | 12/2013 | Schena et al. | |
| 2013/0331644 A1 | 12/2013 | Pandya et al. | |
| 2014/0358162 A1 | 12/2014 | Valdastri et al. | |
| 2015/0081098 A1 | 3/2015 | Kogan | |
| 2015/0237308 A1 | 8/2015 | Tanaka et al. | |
| 2016/0077638 A1 * | 3/2016 | Bulea | G06F 3/044 345/174 |
| 2018/0079074 A1 | 3/2018 | Devengenzo et al. | |
| 2018/0079090 A1 | 3/2018 | Koenig et al. | |

FOREIGN PATENT DOCUMENTS

| | | |
|---|---|---|
| WO | 2018/053360 A1 | 3/2018 |
| WO | 2018/053361 A1 | 3/2018 |

OTHER PUBLICATIONS

Written Opinion of the International Search Authority dated Dec. 1, 2017 for WO Application No. PCT/US17/051922.
Written Opinion of the International Search Authority dated Dec. 1, 2017 for WO Application No. PCT/US17/051908.
Outgoing—ISA/210—International Search Report dated Jan. 23, 2018 for WO Application No. PCT/US17/051921.
Outgoing—ISA/210—International Search Report dated Dec. 1, 2017 for WO Application No. PCT/US17/051922.
Outgoing—ISA/210—International Search Report dated Dec. 1, 2017 for WO Application No. PCT/US17/051908.
Examiner's Report of the Canadian Patent Office dated Jan. 31, 2020, for Canadian application No. 3,034,639.

* cited by examiner

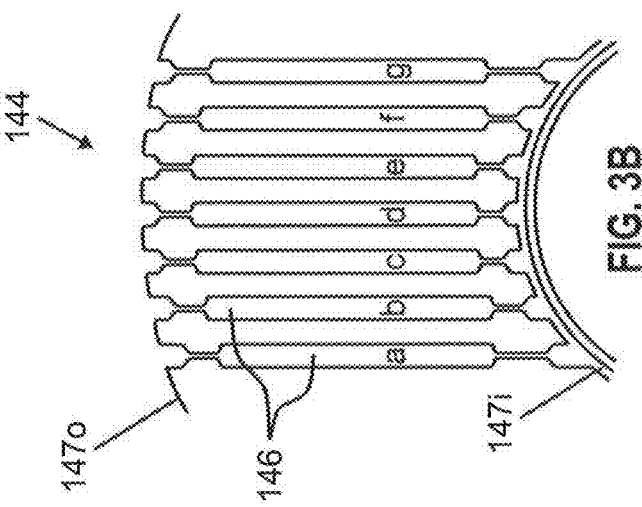
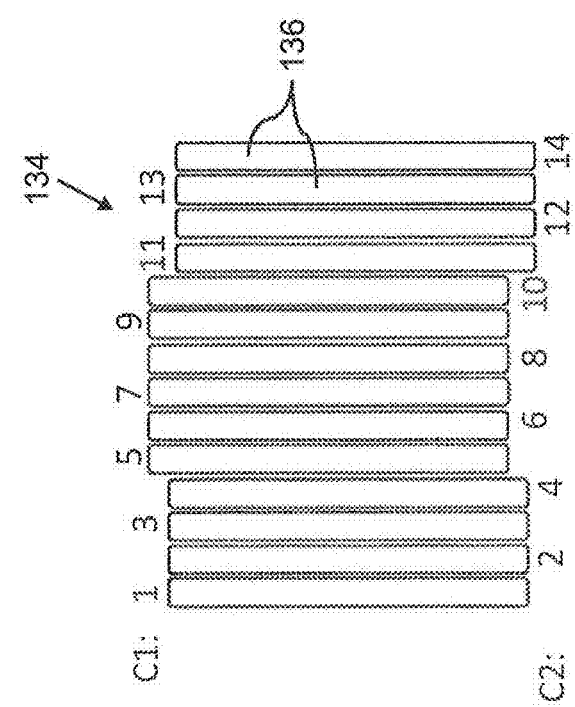
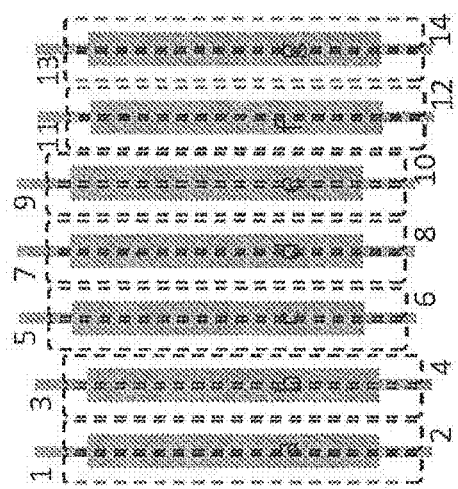
FIG. 3A
FIG. 3B
FIG. 3C

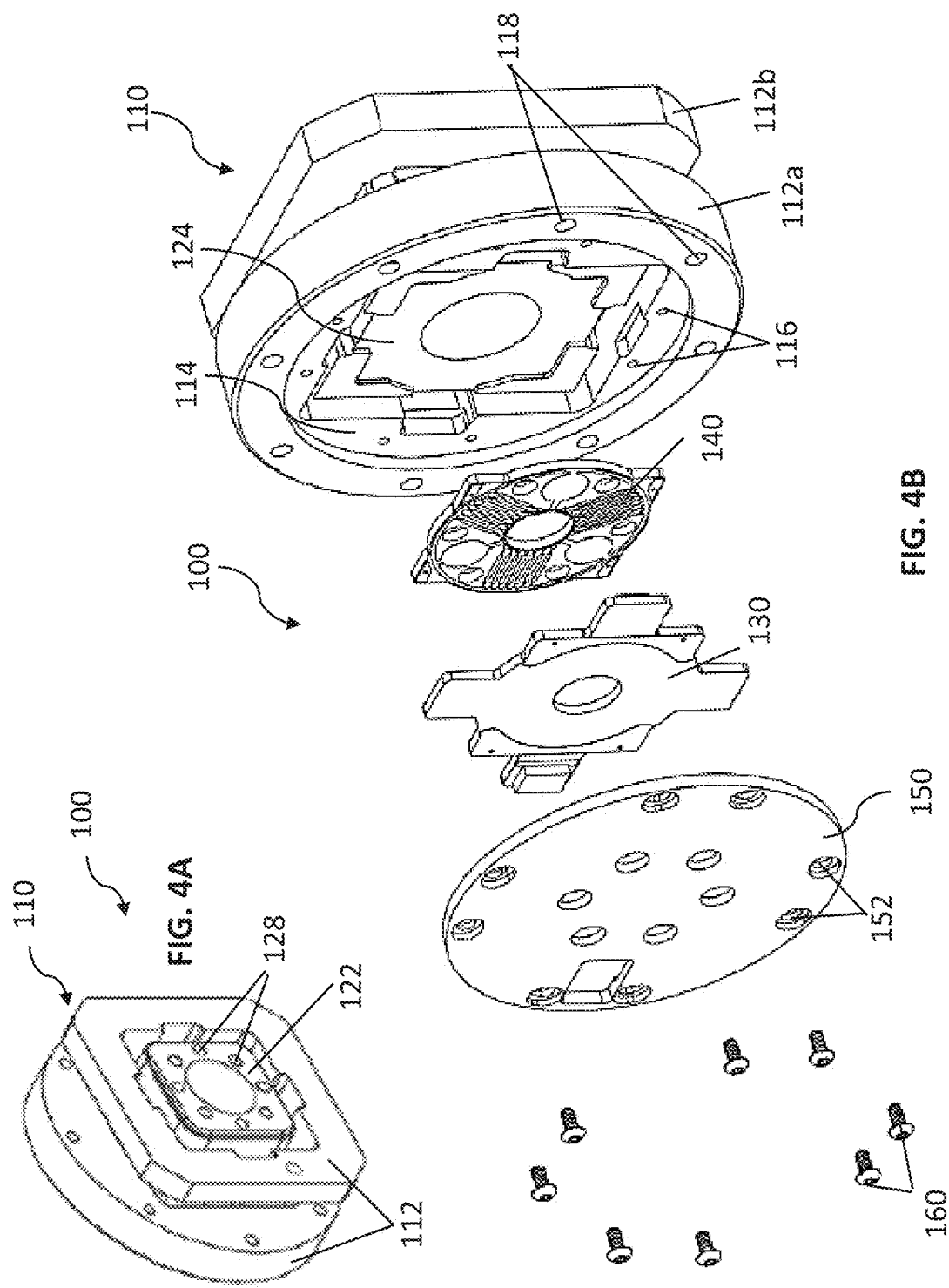

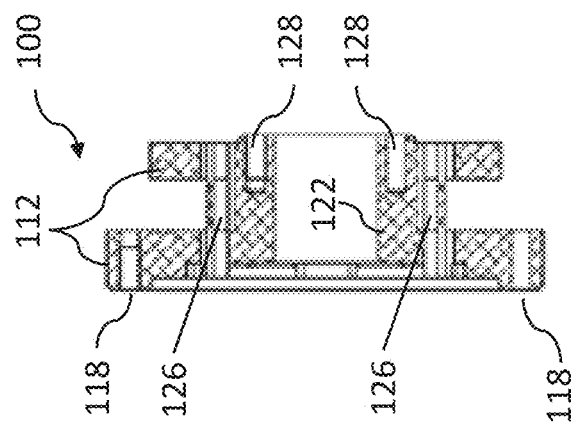
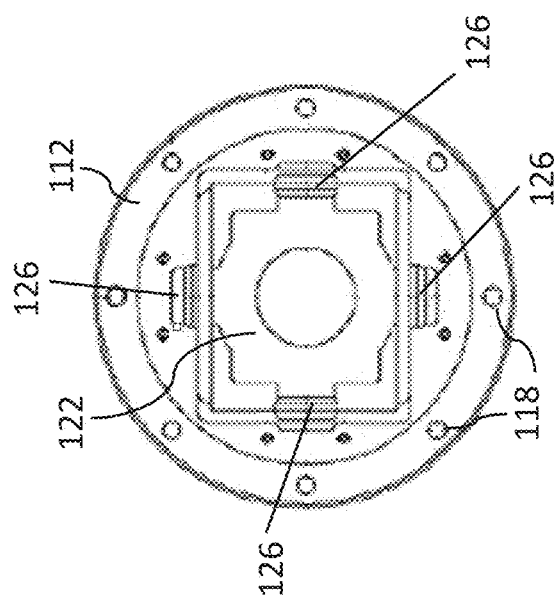

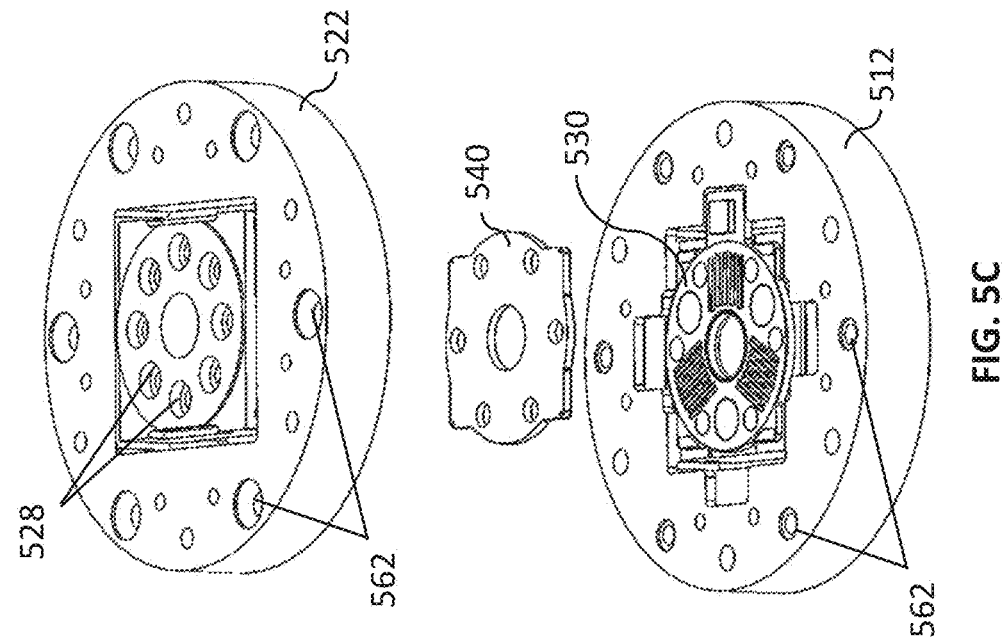
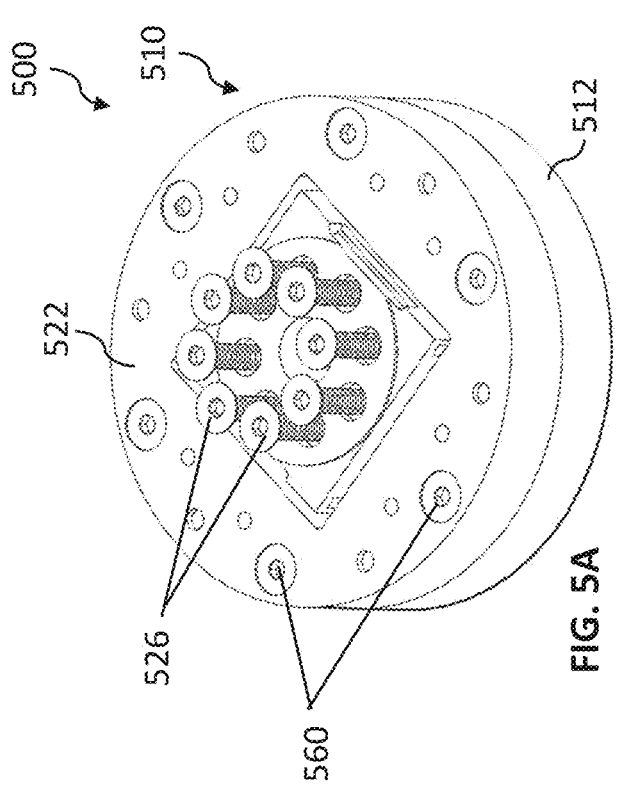
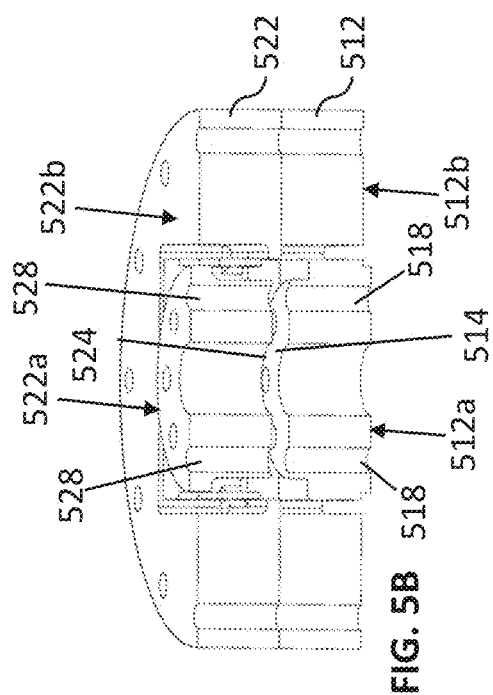
FIG. 5A
FIG. 5B
FIG. 5C

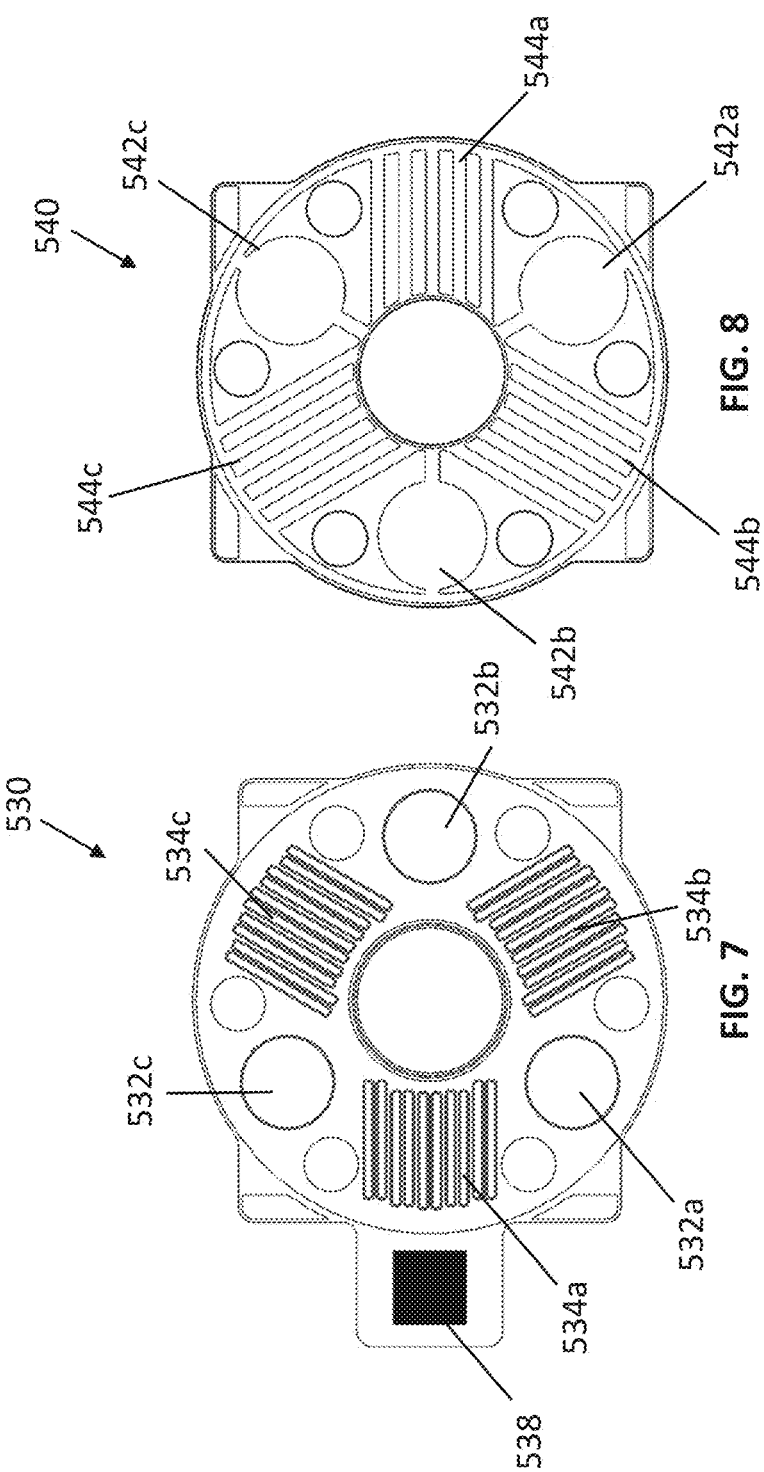

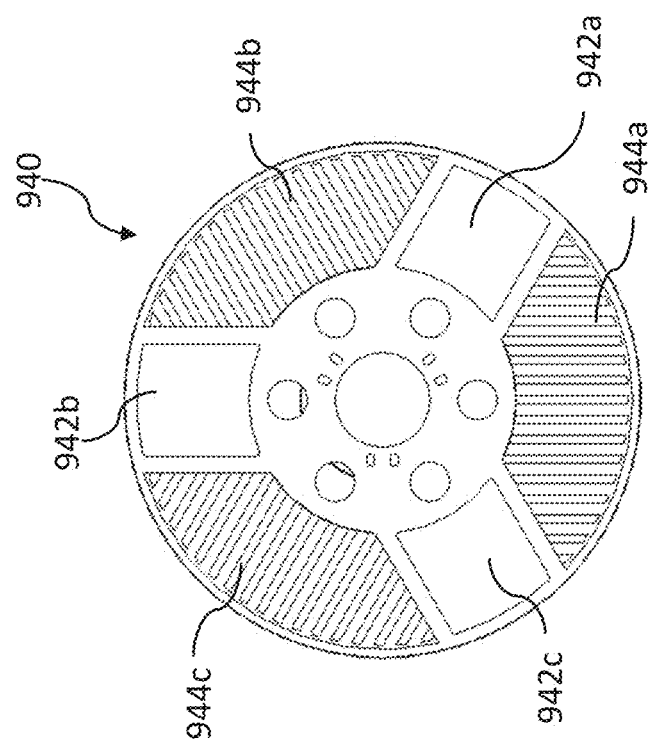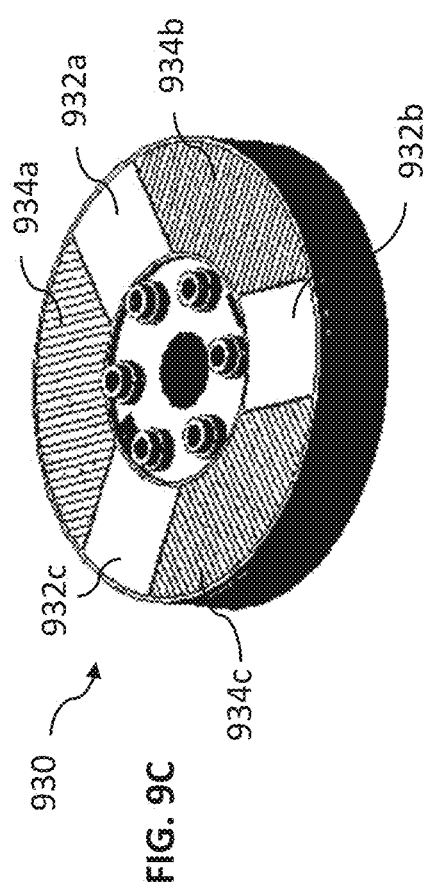
FIG. 9D
FIG. 9C

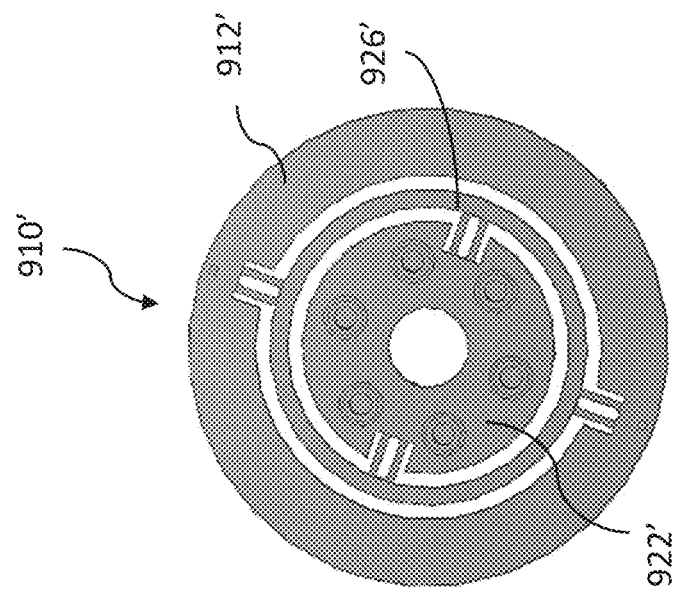
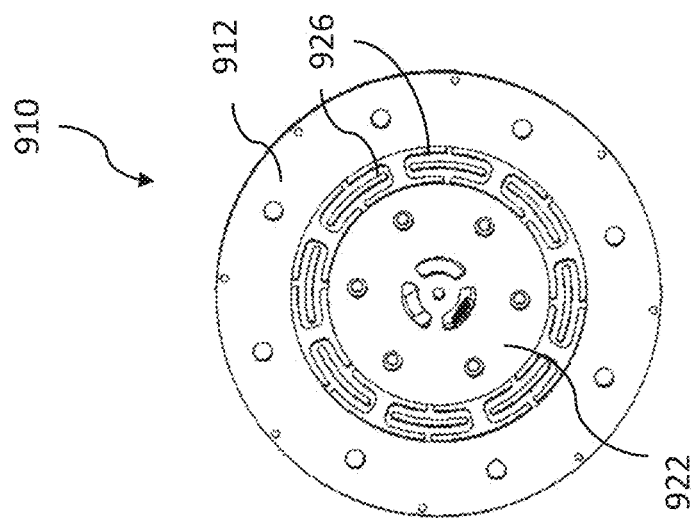

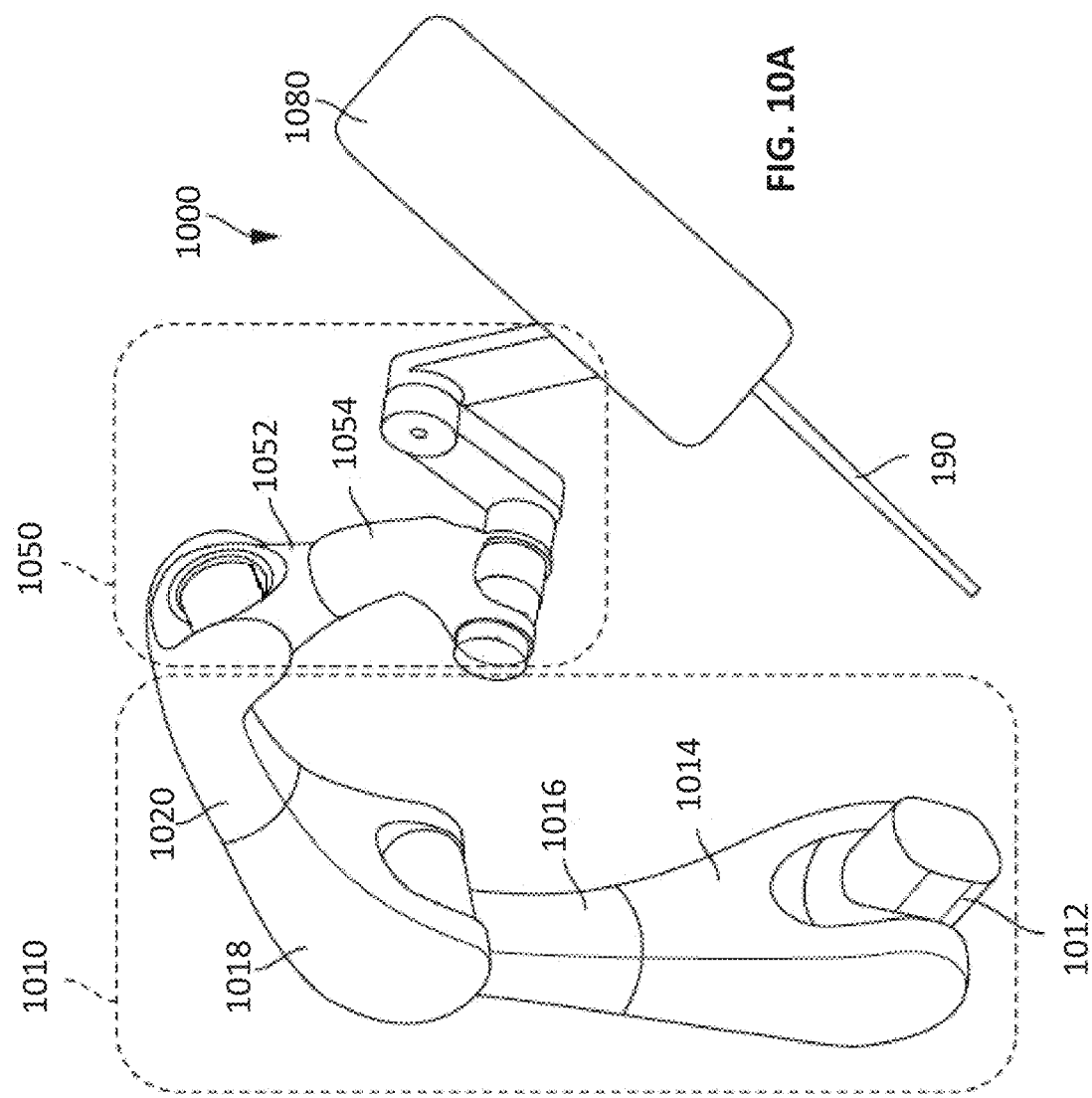

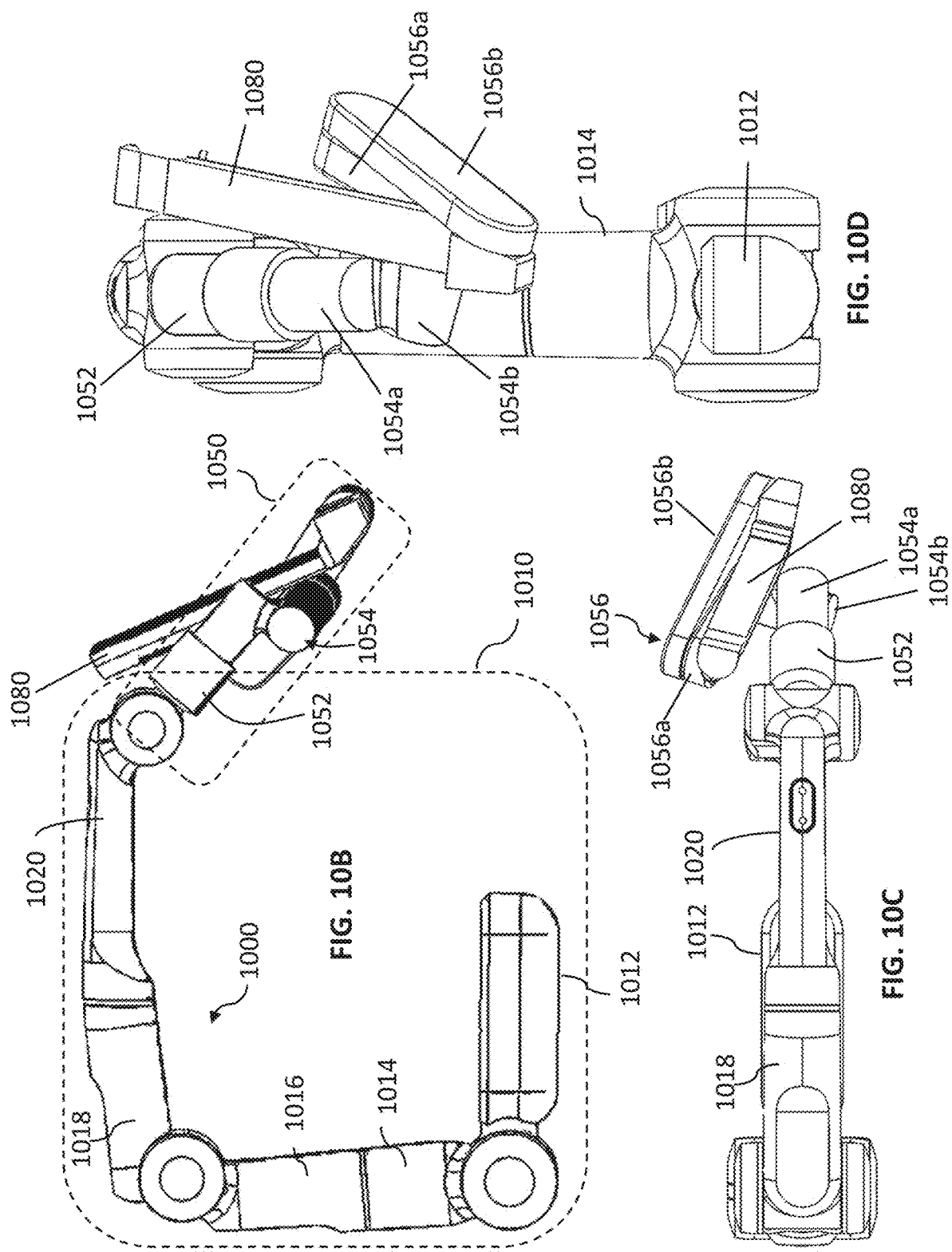

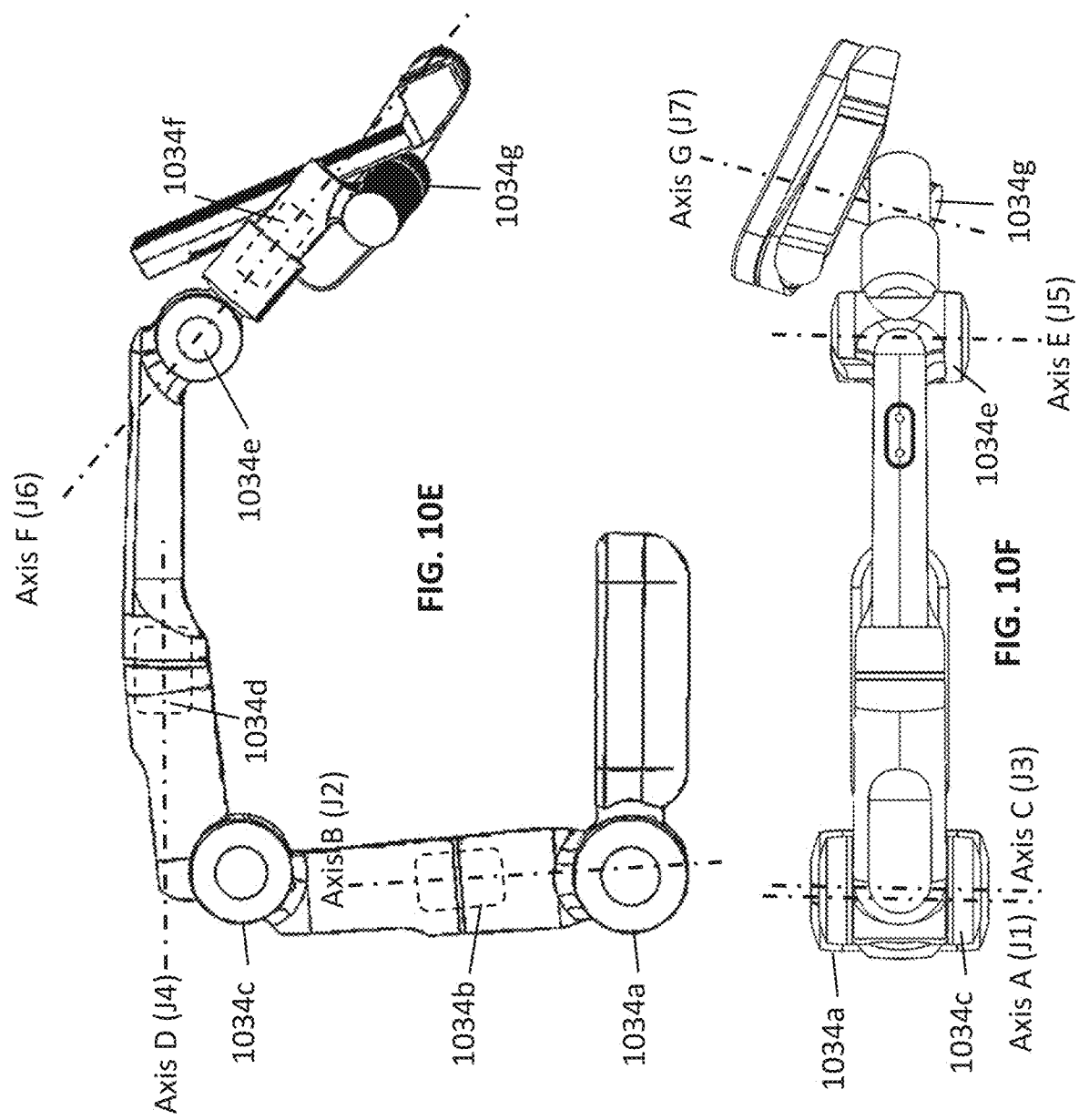

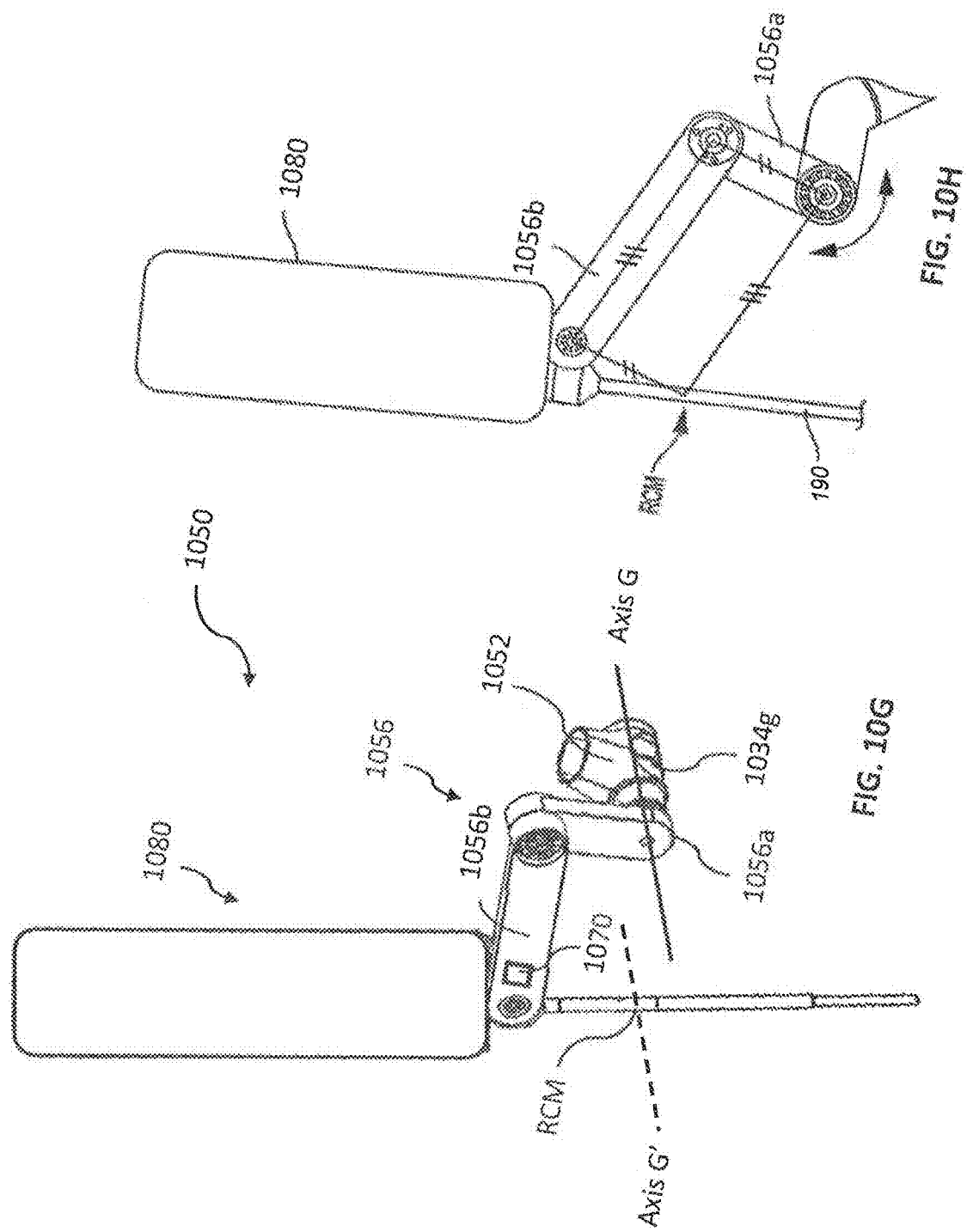

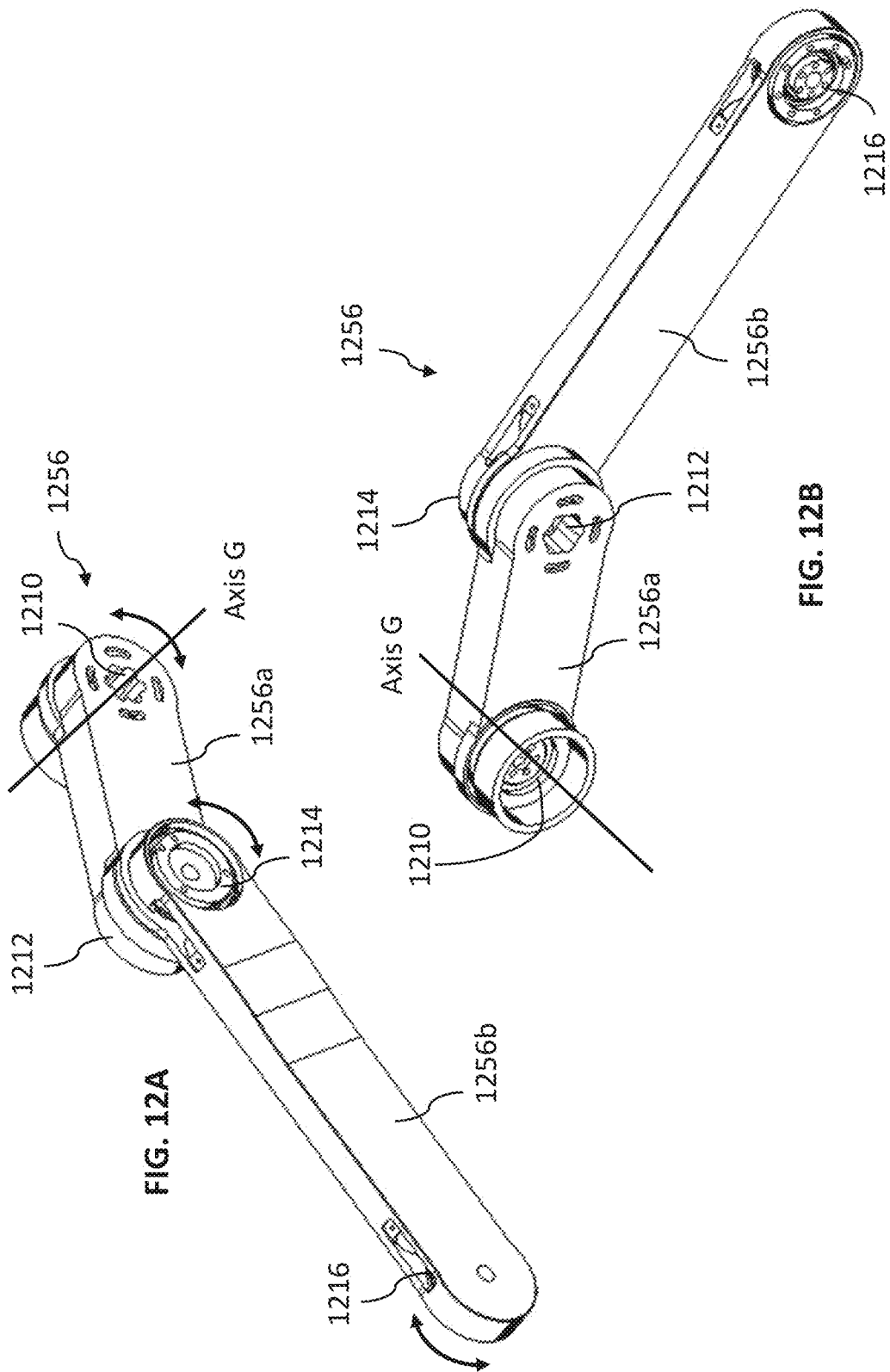

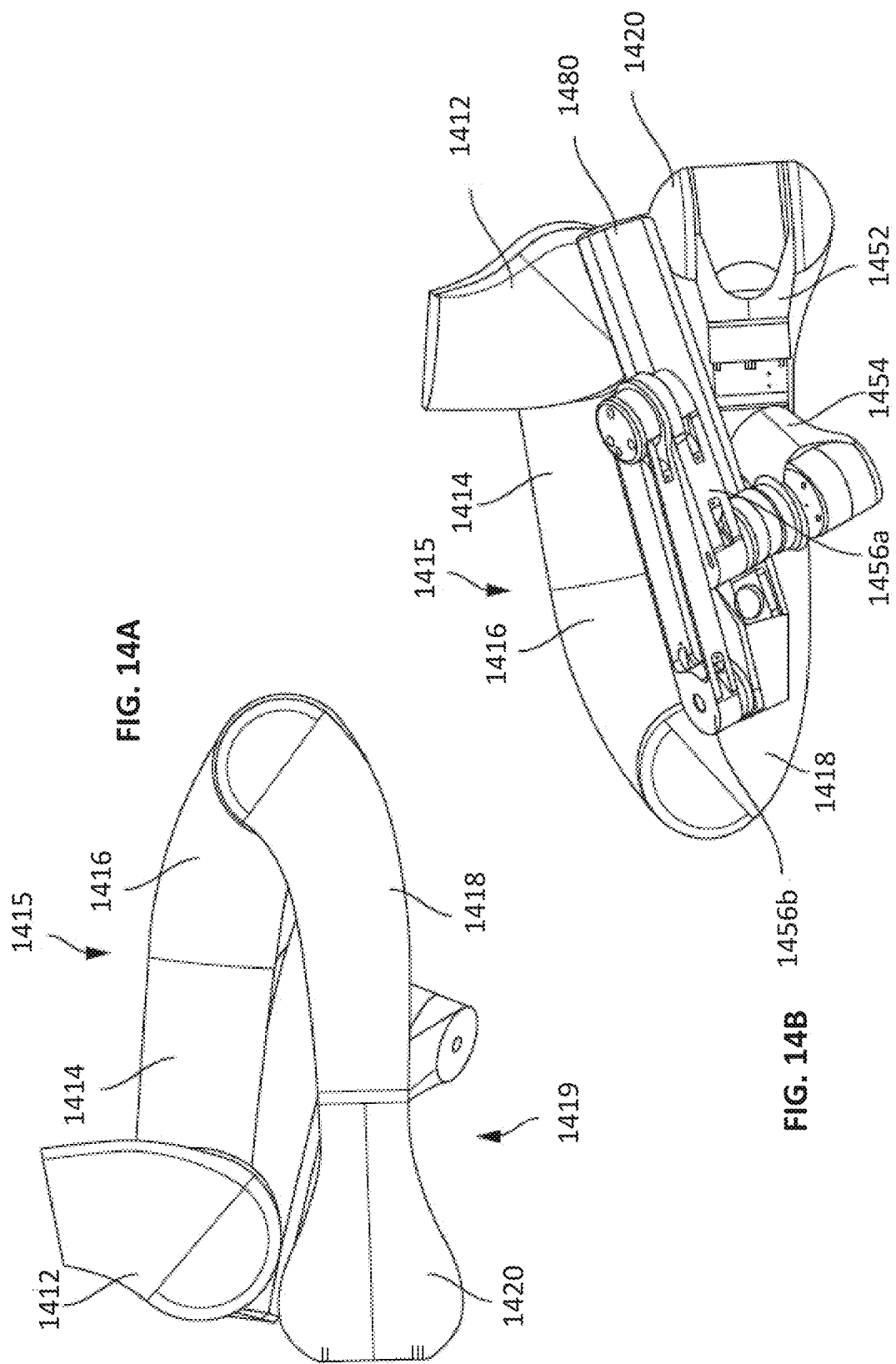

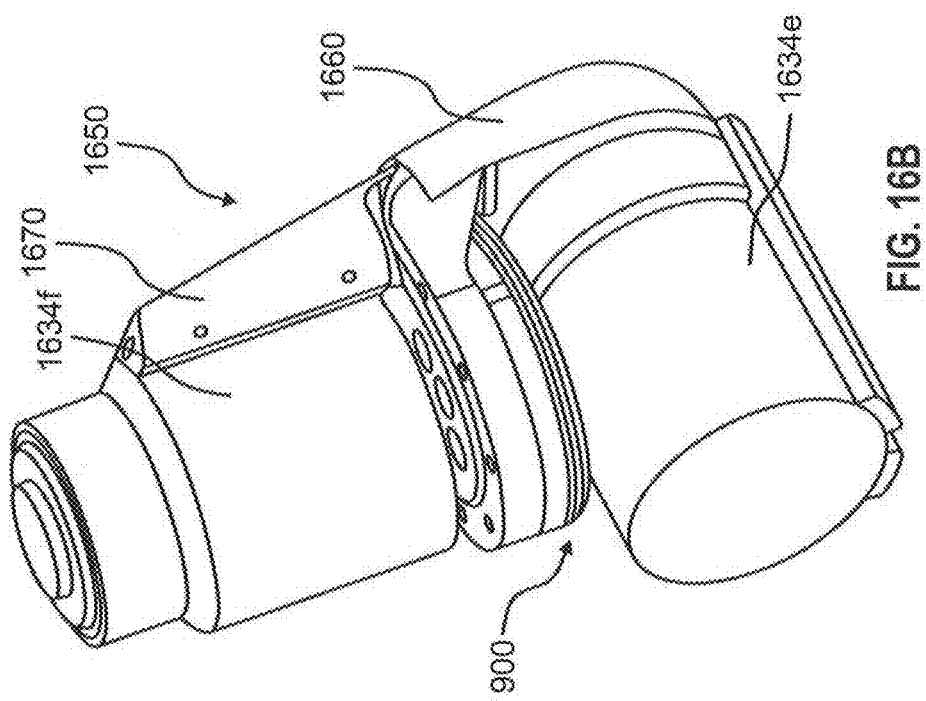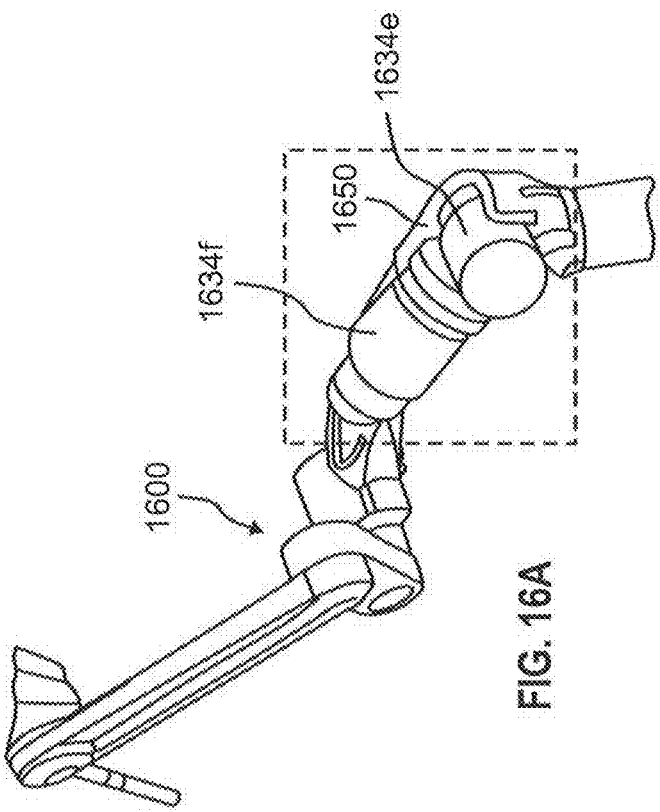

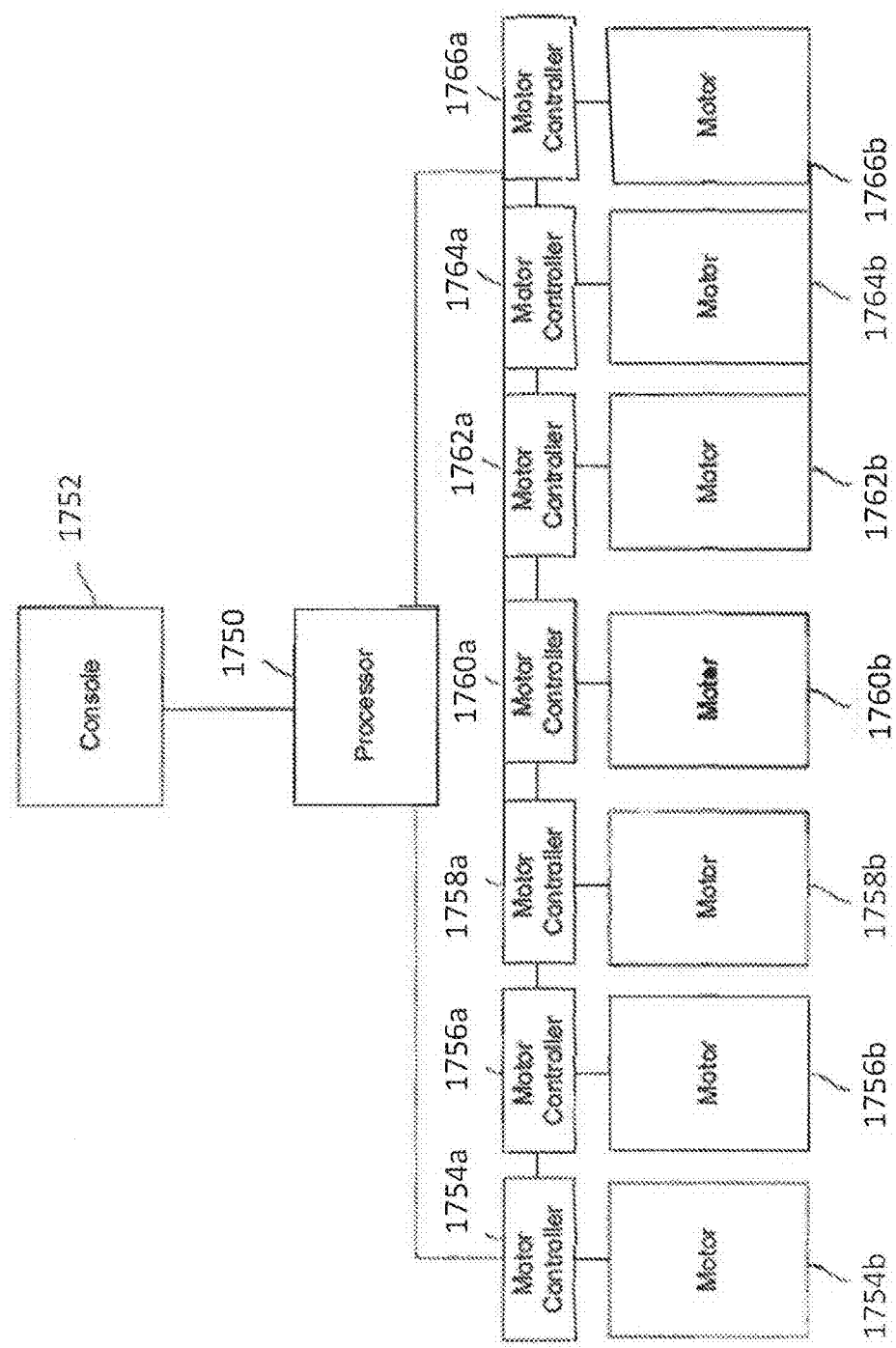

CAPACITOR SENSOR INCLUDING TWO PLATES HAVING BOTH CONDUCTIVE AND NON CONDUCTIVE REGIONS

CROSS-REFERENCE TO RELATED APPLICATIONS

This application claims priority to U.S. Patent Application Ser. No. 62/395,704, filed on Sep. 16, 2016, which is hereby incorporated by this reference in its entirety.

TECHNICAL FIELD

This invention relates generally to the field of sensors, and more specifically to sensors for measuring force and torque.

BACKGROUND

For some mechanical and electromechanical systems, it may be desirable to accurately measure force and/or torque directed along or around multiple different axes or directions. For example, a robotic arm (e.g., for robotic surgery, for manufacturing, etc.) may have multiple degrees of freedom and move in multiple different directions. A robotic arm may be operated with the use of one or more control algorithms. As the robotic arm experiences forces and/or torques in various directions (e.g., as the result of reaction forces or torque), measurements of these forces and/or torques may be applied as inputs to the one or more algorithms for more effective operation of the robotic arm. Accordingly, accurate and precise force and/or torque measurements may be important to successful operation and control of some mechanical and electromechanical systems.

Furthermore, in some kinds of systems, there may be limited available space for sensors and other similar components, and/or limited locations where sensors may be placed to effectively measure force and/or torque in the system. As such, it may be difficult to include multiple sensors, each measuring force or torque in one respective degree of freedom, in a system that requires measurement of force and/or torque in multiple degrees of freedom. Thus, it is desirable to have sensors for measuring force and/or torque in one or more degrees of freedom.

SUMMARY

Generally, a capacitive sensor for characterizing force and/or torque may include a first plurality of non-patterned conductive regions and a first plurality of patterned conductive regions, and a second plurality of non-patterned conductive regions and a second plurality of patterned conductive regions. The first and second pluralities of non-patterned conductive regions may be arranged such that they are facing each other and the first and second pluralities of patterned conductive regions may be arranged such that they are facing each other. For example, the first plurality of non-patterned conductive regions and the first plurality of patterned conductive regions may be disposed on a first surface of the capacitive sensor, and the second plurality of non-patterned conductive regions and the second plurality of patterned conductive regions may be disposed on a second surface, where the first and second surfaces are opposite one another. For example, the first and second surfaces may be disposed on respective plates or other supporting members. The first and second surfaces may be spaced apart from one another (e.g., separated by a gap). The first and second surfaces may be generally axially aligned with one another, but may be arranged in any suitable manner (e.g. an arrangement that orients their conductive regions to be facing each other).

In some variations, the capacitive sensor may measure relative lateral translation and/or relative rotation between the first and second surfaces based at least partially on area of overlap between the first and second pluralities of patterned conductive regions. Additionally and/or alternatively, the capacitive sensor may measure relative axial displacement between the first and second surfaces based at least partially on gap distance between at least one of the first plurality of non-patterned conductive regions and at least one of the second plurality of non-patterned conductive regions.

At least some of the first plurality of patterned conductive regions may be "active" regions and configured to provide capacitive signals, and at least some of the second plurality of patterned conductive regions may be electrical "ground" regions and configured to provide a nominal reference for the capacitive signals (e.g., conductively coupled to a common electrical ground). At least some of the second plurality of non-patterned conductive regions may additionally be conductively coupled to the common electrical ground.

The arrangement and patterning of non-patterned conductive regions and patterned conductive regions may vary. For example, in some variations, at least one of the "active" patterned regions may include at least a first group of conductive strips and a second group of conductive strips. For example, the first group of conductive strips and the second group of conductive strips may be arranged in an alternating pattern on the first surface. The first group of conductive strips may form a first signal channel, and the second group of conductive strips may form a second signal channel. Furthermore, in some variations, at least one of the "ground" patterned regions may include at least a third group of conductive strips. The third group of "ground" conductive strips may face a portion of the first group of "active" conductive strips and a portion of the second group of "active" conductive strips. In some variations, the capacitive sensor may further include at least one reference conductive pad (e.g., disposed on at least one of the first and second plates).

As another example, the first plurality of patterned conductive regions may be additionally or alternatively arranged around a center point on the first surface. The first plurality of patterned conductive regions may be arranged equally distributed from one another around the center point. For example, in a variation in which the first plurality of patterned conductive regions on a first surface includes three patterned conductive regions, the three patterned conductive regions may be arranged approximately 120 degrees from one another around the center point.

In some variations, the capacitive sensor may further include a base including a first base portion and a second base portion that are movable relative to one another (rotationally displaceable, laterally displaceable, and/or axially displaceable, in out-of-plane and/or in-plane directions). For example, the first and second base portions may form a torsional spring and/or a linear spring. The first plurality of non-patterned conductive regions and the first plurality of patterned conductive regions may be fixed relative to the first base portion of the base. The second plurality of non-patterned conductive regions and the second plurality of patterned conductive regions may be fixed relative to the second base portion of the base. Furthermore, in some variations, the capacitive sensor may further include a cover configured to couple to the base such that the cover and the base enclose the first and second surfaces.

BRIEF DESCRIPTION OF THE DRAWINGS

FIGS. 3A-3C depict patterned conductive regions in one exemplary variation of a multi-DOF capacitive sensor. FIG. 3A is a schematic illustration of one patterned conductive region including two signal channels. FIG. 3B is a schematic illustration of one patterned conductive region conductively coupled to a common electrical ground. FIG. 3C is a schematic illustration of the patterned conductive regions depicted in FIGS. 3A and 3B, when the patterned conductive regions are facing each other.

FIGS. 4A and 4B are a perspective view and an exploded view, respectively, of one exemplary variation of a multi-DOF capacitive sensor. FIGS. 4C and 4D are front and side views, respectively, of a base in the sensor variation depicted in FIGS. 4A and 4B.

FIGS. 5A-5C are a perspective view, a side cross-sectional view, and an exploded view, respectively, of another exemplary variation of a multi-DOF capacitive sensor.

FIGS. 7 and 8 are schematic illustrations of plates with non-patterned conductive regions and patterned conductive regions in another exemplary variation of a multi-DOF capacitive sensor.

FIGS. 9A-9I depict aspects of another exemplary variation of a multi-DOF capacitive sensor. FIGS. 9A and 9B are an exploded view and an assembled view, respectively, of the sensor variation. FIGS. 9C and 9D are schematic illustrations of plates with non-patterned conductive regions and patterned-conductive regions in the sensor variation. FIGS. 9E and 9F are exemplary variations of a base in the sensor variation. FIG. 9G is a side cross-sectional view of the sensor variation. FIGS. 9H and 9I are perspective and detailed views, respectively, of the conductive regions in the sensor variation.

FIG. 10A-10H are schematic illustrations of one exemplary variation of a robotic arm.

FIGS. 12A and 12B are schematic illustrations of one exemplary variation of a spherical pitch assembly for a robotic arm.

FIGS. 14A and 14B are schematic illustrations of exemplary folded configurations of a variation of a robotic arm.

FIG. 16A is an exemplary variation of a robotic arm including a multi-DOF capacitive sensor and a sensor mount coupling the capacitive sensor to the robotic arm. FIG. 16B is a perspective view of the sensor mount depicted in FIG. 16A.

FIG. 17 is an overview schematic of an exemplary control system setup for controlling actuation of the joint modules of one variation of a robotic arm.

DETAILED DESCRIPTION

Non-limiting examples of various aspects and variations of the invention are described herein and illustrated in the accompanying drawings.

Multi-DOF Capacitive Sensor Variations

In some variations, In one aspect, provided herein is a capacitive sensor may characterize up to six degrees of freedom (DOFs) of relative motion between two surfaces or components, including translation along an X-axis, translation along a Y-axis, translation along a Z-axis, rotation around a roll axis, rotation around a pitch axis, and rotation around a yaw axis (e.g., three directions of force and three directions of torque). For example, as described below in an exemplary application, such a six DOF capacitive sensor may be disposed between adjacent links of a robotic arm or other multi-segmented manipulator, and may characterize six DOFs (three directions of force and three directions of torque) by measuring small displacements between the two adjacent links. For example, as described in further detail below, the force and/or torque measurements provided by the six DOF capacitive sensor may serve as inputs into a virtual model of the robotic arm, where the response of the virtual model to the force/torque inputs forms the basis of the actuator commands for the robotic arm according to one or more control algorithms. However, the six DOF capacitive sensor may be included in any suitable kind of system.

As further described herein, the multi-DOF capacitive sensor may provide simultaneous, accurate, and precise measurement of force and/or torque in any DOF up to six DOF, in a compact, low-volume assembly such that the multi-DOF capacitive sensor provides for more functionality in a smaller arrangement compared to conventional sensors. Accordingly, the multi-DOF capacitive sensor may be used in, for example, systems that require force and/or torque measurements but have various space and/or weight restrictions (e.g., robotic surgical systems).

Figure 2:
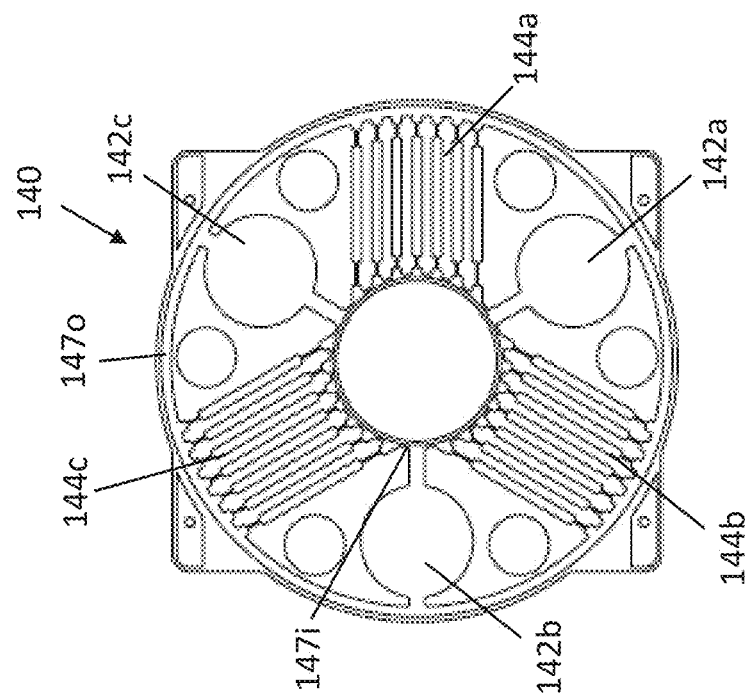
FIGS. 1 and 2 are schematic illustrations of plates with non-patterned conductive regions and patterned conductive regions in one exemplary variation of a multi-degree of freedom (DOF) capacitive sensor.
Figure 1:
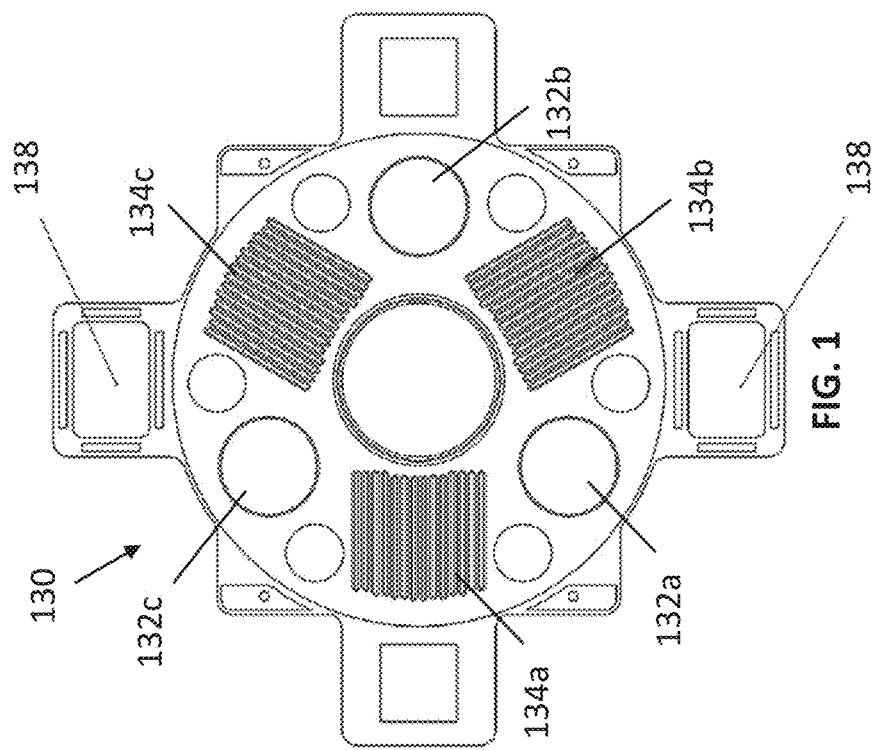

Generally, in some variations, the capacitive sensor for characterizing force or torque may include a first plurality of non-patterned conductive regions (e.g., $132a$-$132c$ as shown in FIG. 1) and a first plurality of patterned conductive regions (e.g., $134a$-$134c$ as shown in FIG. 1); and a second plurality of non-patterned conductive regions (e.g., $142a$-$142c$ as shown in FIG. 2) and a second plurality of patterned conductive regions (e.g., $144a$-$144c$ as shown in FIG. 2). The first and second pluralities of non-patterned conductive regions may be facing each other and the first and second pluralities of patterned conductive regions may be facing each other. As shown, for example, in FIG. 4B, the first pluralities of non-patterned and patterned conductive regions may be disposed on a first surface (hidden in FIG. 4B) on a first plate 130, and the second pluralities of non-patterned and patterned conductive regions may be disposed on a second surface on a second plate 140, with the first surface and second surface facing each other.

One of the first and second surfaces (e.g., the first surface) may function as an "active" surface having multiple discrete conductive regions, with each discrete "active" region including at least one separate signal channel. The other surface (e.g., the second surface) may function as a "ground" surface having conductive "ground" regions that are conductively coupled to a common electrical ground. Alternatively, the first surface and/or second surfaces may include a mixture of "active" and "ground" conductive regions, with "active" regions on one surface facing or opposing "ground" regions on the other surface. Absolute values of capacitance measurement and/or changes in capacitance measurements between the facing non-patterned regions and between the facing patterned regions may be used to characterize motion in up to six DOF between the "active" and the "ground" surfaces.

For example, as further described herein, the capacitive sensor may measure or otherwise characterize relative axial displacement (e.g., along a Z-axis) and/or relative out-of-plane rotation (e.g. yaw or pitch) between the first and second surfaces based at least partially on gap distance between one or more of the first plurality of non-patterned conductive regions and one or more of the second plurality of non-patterned conductive regions. As another example, the capacitive sensor may measure or otherwise characterize relative lateral translation (e.g., along an X-axis and/or a Y-axis) and/or relative planar rotation (e.g., roll) between the first and second surfaces based at least partially on area of overlap between the first and second pluralities of patterned conductive regions. The characterization of these motions based on different combinations of capacitance readings is further described below with reference to exemplary variations of the multi-DOF capacitive sensor.

Generally, in some variations, the capacitive sensor may further include a base that is configured to provide structural support to the various non-patterned and patterned conductive regions of the capacitive sensor. As shown, for example, in FIG. 4A, a base 110 may include a first base portion 112 and a second base portion 122. The first and second base portions may be rotationally moveable, laterally moveable, and/or axially movable relative to each other in out-of-plane and/or in-plane directions. As shown in FIG. 4B, the first plate 130 (on which the first pluralities of non-patterned and patterned conductive regions may be disposed) may be coupled to a surface 114 on the first base portion 112. The second plate 140 (on which the second plurality of non-patterned and patterned conductive regions may be disposed) may be coupled to a surface 124 on the second base portion 122. The first and second plates may be arranged such that their conductive regions are facing. Accordingly, the base portions 112 and 114 may support a relative rotational movement, lateral movement, and/or axial movement between the first plate 130 and the second plate 140, and consequently may facilitate the same relative movement between the first pluralities of non-patterned and patterned conductive regions and the same relative movement between the second pluralities of non-patterned and patterned conductive regions.

Other exemplary variations of conductive regions and variations of a base are further described herein. However, it should be understood that in other variations, the multi-DOF capacitive sensor may include other suitable patterns and arrangement of conductive regions. Additionally or alternatively, other variations of the multi-DOF capacitive sensor may include other suitable variations of a base with relatively displaceable parts that support the relative rotational movement, lateral movement, and/or axial movement of the first pluralities of conductive regions and the second pluralities of conductive regions.

One exemplary variation of a multi-DOF capacitive sensor 100 is shown in FIGS. 1-4D. As best shown in FIG. 1, the capacitive sensor 100 includes a first plate 130 including a first plurality of non-patterned conductive regions 132a-132c and a first plurality of patterned conductive regions 134a-134c. As best shown in FIG. 2, the capacitive sensor 100 further includes a second plate 140 including a second plurality of non-patterned conductive regions 142a-142c and a second plurality of patterned conductive regions 144a-144c. FIGS. 1 and 2 illustrate a variation in which there are three conductive regions in each plurality of non-patterned conductive regions and each plurality of patterned conductive regions. However, it should be understood that any suitable number of conductive regions may be included in each plurality of non-patterned conductive regions and each plurality of patterned conductive regions.

As shown in FIG. 1, one or more of the first plurality of non-patterned conductive regions 132a-132c may include a solid or substantially solid conductive pad covering a non-patterned, uninterrupted surface area of conductivity. For example, the regions 132a-132c shown in FIG. 1 are generally circular or a polygon approximating the shape of a circle (e.g., to avoid inaccuracies or other edge effects due to corners in the shape of the non-patterned conductive regions, etc.), though may alternatively be square, rectangular, pentagonal, etc. or any suitable polygonal shape. In some variations, one or more of the non-patterned conductive regions may cover a surface area of at least about 1 cm$^2$, at least about 1.5 cm$^2$, at least about 2 cm$^2$, or at least about 3 cm$^2$. However, dimensions of the non-patterned conductive regions may vary depending on factors such as the overall desired size of the capacitive sensor, desired signal range and/or sensitivity of the capacitive sensor, etc. In some variations, the conductive regions may include copper, ceramic, or other suitable conductive material. For example, in some applications, the conductive material may be suitably stable under various environmental conditions (e.g., less sensitive to deformation due to temperature, etc.).

One or more of the first plurality of patterned conductive regions 134a-134c may include one or more conductive pads covering a surface area in a patterned, discontinuous manner. For example, as show in FIG. 3A, a patterned conductive region 134 may include a plurality of conductive strips 136 sequentially labeled 1-14. A first group of these conductive strips may be conductively coupled to one another to form a first channel C1, while a second group of these conductive strips may be conductively coupled to one another to form a second channel C2. The strips of the first and second groups of conductive strips may be arranged in an alternating or interleaved manner. For example, the odd-numbered conductive strips (1, 3, 5, 7, 9, 11, and 13) may be conductively connected to form a first channel C1, while the even-numbered conductive strips (2, 4, 6, 8, 10, 12, and 14) that are interleaved between the odd-numbered conductive strips form a second channel C1.

Although the variation shown in FIG. 3A shows an exemplary patterned conductive region having fourteen conductive strips, it should be understood that other variations of a patterned conductive region may include fewer (e.g., any of two through twelve) or more (e.g., any of fourteen through twenty, or more) conductive strips. Furthermore, the conductive strips may be generally linearly-shaped, though in other variations, the conductive strips in a patterned conductive region may be curvilinear (e.g., sine waves or other curved lines) or any suitable shape. In yet other variations, a patterned conductive region may include other suitable patterns. For example, a patterned conductive region may include a pattern of conductive elements (e.g., conductive pads that are conductively coupled to form a first channel and a separate second channel) where the pattern is substantially regularly repeated across the surface area of the patterned conductive region (e.g. checkered, polka dots, etc.).

As shown in FIG. 1, the first plurality of non-patterned conductive regions 132a-132c may be arranged in a radially symmetric manner on a first surface (e.g., on the first plate 130). For example, three non-patterned conductive regions may be equally distributed around a center point of the first plate 130, or arranged about 120 degrees apart from each other. Similarly, the first plurality of patterned conductive regions 134a-134c may be arranged in a radially symmetric manner on the first surface (e.g., on the first plate 130). For example, three patterned conductive regions may be equally distributed around the center point of the first plate 130, or arranged about 120 degrees apart from each other. The first plurality of non-patterned conductive regions 132a-132c and the first plurality of patterned conductive regions 134a-134c may be arranged around the first plate 130 in an alternating manner.

As shown in FIG. 2, one or more of the second plurality of non-patterned conductive regions 142a-142c may include a solid or substantially solid conductive region similar to the regions 132a-132c except that the non-patterned conductive regions 142a-142c may be conductively coupled to each other through conductive traces or other electrical connection. For example, the non-patterned conductive regions 142a-142c may be conductively connected to each other as a common electrical ground. As shown in FIG. 2, the non-patterned conductive regions 142a-142c are conductively coupled via an inner ring-shaped trace 147i and an outer ring-shaped trace 147o, though in other variations the non-patterned conductive regions may be conductively coupled with any suitable pattern of traces (e.g., other suitable conductive trace networks on the surface of the plate). Like the non-patterned conductive regions 132a-132c on the first plate 130, the non-patterned conductive regions 142a-142c may be equally distributed on the second plate 140.

One or more of the second plurality of patterned conductive regions 144a-144c may include one or more conductive pads covering a surface area in a patterned manner similar to regions 142a-14c, except that the conductive elements of the second plurality of patterned conductive regions 144a-144c may be conductively coupled to each other and to the second plurality of non-patterned conductive regions 142a-142c. For example, as shown in more detail in FIG. 3B, a patterned conductive region 144 may include a group of conductive strips 146, sequentially labeled "a" through "g". The conductive strips 146 may be connected to each other and/or to the second plurality of non-patterned conductive regions 142-142c via the inner ring-shaped trace 147i and the outer ring-shaped trace 147o. However, such connections may be achieved with any suitable pattern of traces (e.g., other suitable conductive trace networks on the surface of the plate). Like the patterned conductive regions 134a-134c on the first plate 130, the non-patterned conductive regions 144a-144c may be equally distributed from one another on the second plate 140.

In the capacitive sensor 100, the first plate 130 and the second plate 140 may be facing each other such that each of the first plurality of non-patterned conductive regions 132a-132c on the first plate may be facing a respective region in the second plurality of non-patterned conductive regions 142a-142c on the second plate. In some variations, the non-patterned conductive regions 132a-132c and the non-patterned conductive regions 142a-142c may be sized and/or arranged in such a way that as the first and second plates translate and/or rotate in-plane relative to each other (e.g., in an X-direction, in a Y-direction, or in roll), the surface area of overlapping non-patterned regions does not change significantly. For example, the second plurality of non-patterned conductive regions 142a-142c may be larger than the first plurality of non-patterned conductive regions 132a-132c, such that the regions 132a-132c may move in-plane relative to the regions 142a-142c up to a certain amount without decreasing the amount of overlapping area between the regions 132a-132c and the regions 142a-142c. For example, each of the second plurality of non-patterned conductive regions 142a-142c may cover between about 1 and about 4 times, between about 1 and about 3, between about 1 and about 2, or between about 1 and about 1.5 times, the surface area of its mutually facing non-patterned conductive region in the first plurality of non-patterned conductive regions 132a-132c.

Furthermore, the first plate 130 and the second plate 140 may be facing such that each of the first plurality of patterned conductive regions 134a-134c may be facing a respective region in the second plurality of patterned conductive regions 144a-144c. In some variations, the patterned conductive regions 134a-134c and the patterned conductive regions 144a-144c may be sized and/or arranged such that when the plates 130 and 140 are in a nominal position (e.g., not experiencing relative in-plane movement), each of the conductively-connected patterned elements in the regions 144a-144c may face (e.g., overlap with, be disposed over, etc.) at least two conductively discrete patterned elements among the patterned regions 134a-134c (e.g., at one patterned element from each channel C1 and C2). In some variations, when the capacitive sensor is in a nominal position, each patterned element in the second plurality of patterned conductive regions 144a-144c may overlap with (e.g., face or be in opposition with) two discrete patterned elements in the first plurality of patterned conductive regions 134a-134c about equally. For example, as shown in FIG. 3C, the strip labeled "a" (in the second plurality of patterned conductive regions) overlaps about half of strip 1 and half of strip 2 (both in the first plurality of patterned conductive regions). The strip labeled "b" overlaps about half of strip 2 and about half of strip 3, and so on.

Generally, in the above-described arrangement of conductive regions in the capacitive sensor 100, the signals from the non-patterned conductive regions 132a-132c on the first plate 130 and/or the non-patterned conductive regions 142a-142c on the second plate 140 may be sensitive to gap size variations between the first plate 130 and the second plate 140. Accordingly, the capacitive sensor 100 may determine relative axial movement (e.g., in a Z-direction) between the first and second plates based at least partially on detected or measured gap distance between at least one of the non-patterned conductive regions 132a-132c and at least one of the non-patterned conductive regions 142a-142c. For example, if an external force acts axially to compress the first and second plates together, the relative axial displacement of the first and/or second plates (or reduction in gap distance) may be measurable by detecting the resulting change in capacitance primarily from the non-patterned pads (e.g., since there is significantly greater conductive surface area in the non-patterned regions than in the patterned regions). In other words, for a particular pair of facing non-patterned conductive regions $A_1$ and $A_2$ (e.g., region 132a on the first plate 130 and region 142a on the second plate 140, respectively), the measured capacitance $C_{A1,A2}$ between the conductive regions $A_1$ and $A_2$ is generally inversely proportional to the gap distance $d_{A1,A2}$ between the conductive regions $A_1$ and $A_2$ as shown, for example, in Equation 1 below:

$$C_{A1,A2} \propto \frac{1}{d_{A1,A2}} \quad (1)$$

Similarly, changes in measured capacitances in other pairs of facing non-patterned conductive regions on the first and second plates may be measured. For example, a second pair of facing non-patterned conductive regions $B_1$ and $B_2$ (e.g., region 132b on the first plate 130 and region 142b on the second plate 140, respectively) may provide a measured capacitance $C_{B1,B2}$ between the conductive regions $B_1$ and $B_2$ that is inversely proportional to the gap distance $d_{B1,B2}$ between the conductive regions $B_1$ and $B_2$. A third pair of facing non-patterned conductive regions $C_1$ and $C_2$ (e.g., region 132c on the first plate 130 and region 142c on the second plate 140, respectively) may provide a measured capacitance $C_{C1,C2}$ between the conductive regions $C_1$ and $C_2$ that is inversely proportional to the gap distance $d_{C1,C2}$ between the conductive regions $C_1$ and $C_2$, etc.

By comparing the relative changes in the measured capacitances $C_{A1,A2}$, $C_{B1,B2}$, and $C_{C1,C2}$, etc., relative axial translation and/or out-of-plane rotation between the first plate 130 and the second plate 140 may be determined and mapped. For example, if the change among all the measured capacitances are generally equal (e.g., equal within a predetermined threshold), then it may be determined that the changes are due to the first and second plates moving axially closer together (if capacitance has increased) or axially apart (if capacitance has decreased), with the first and second plates remaining parallel. The extent of such axial translation may be correlated to the magnitude of the change in capacitance. As another example, if the change among at least one measured capacitance is greater than another measured capacitance (e.g., greater than a predetermined threshold), then it may be determined that the changes are due to relative out-of-plane rotation (e.g., tilting in yaw and/or pitch). Direction of the out-of-plane rotation (e.g., magnitude of yaw and/or pitch) may be determined by comparing relative changes in the measured capacitances $C_{A1,A2}$, $C_{B1,B2}$, and $C_{C1,C2}$. As an illustrative example only, if $C_{A1,A2}$ increases while $C_{B1,B2}$ and $C_{C1,C2}$ decrease, it may be determined that the first and second plates 130 and 140 have rotated out-of-plane relative to each other to move conductive regions $A_1$ and $A_2$ closer together, conductive regions $B_1$ and $B_2$ farther apart, and conductive regions $C_1$ and $C_2$ farther apart. The extent of such tilting is correlated to the magnitude of the changes in capacitance. Other directions and magnitudes of out-of-plane rotation in yaw, pitch, or both, may be determined based on the direction and magnitude of relative capacitance increases and/or relative capacitance decreases.

Furthermore, generally, in the above-described arrangement of conductive regions in the capacitive sensor 100, the signals from the patterned conductive regions 134a-134c on the first plate 130 and/or the patterned conductive regions 144a-144c on the second plate 140 may be sensitive to detecting relative in-plane motion of the first and second plates. For example, the capacitive sensor 100 may determine relative lateral movement (e.g., in an X-direction and/or Y-direction, or in-plane rotation) between the first plate 130 and the second plate 140 based at least partially on the detected area of the patterned regions 134a-134c on the first plate 130 that overlap with the patterned regions 144a-144c on the second plate 140.

For example, if an external force acts to move the first plate 130 laterally relative to the second plate 140 (e.g., to cause the first and second plates to be axially misaligned), then the relative lateral displacement of the first and second plates may be measurable by detecting the resulting change in capacitance primarily from certain patterned regions. As another example, if an external force acts to rotate the first plate 130 relative to the second plate 140 (e.g., around a common axis), then the relative rotational displacement of the first and second plates may additionally or alternatively be measurable by detecting the resulting change in capacitance primarily from certain patterned regions. Mapping which patterned pads are providing a change in signal may indicate the direction of the relative lateral displacement and/or in-plane rotation between the plates 130 and 140. The magnitude of the change(s) in signal may indicate the extent of the relative lateral displacement and/or in-plane rotation. One of the plates may be an "active" or "sensor" plate, while the other plate may be a "ground" plate. The "active" plate may further include electronics for measuring capacitance between the first and second plates (although alternatively signals from the "active" conductive regions may be passed to electronics located in any suitable location, such as on the "ground" plate, the base 110 or other suitable housing).

As one illustrative example, referring to FIGS. 3A-3C, relative rotation of the first plate 130 (including a patterned conductive region 134 with conductive strips 136) and the second plate 140 (including a patterned conductive region 144 with conductive strips 146) causes both a shift in the amount of overlapping area between the regions 134 and 144, and a shift in which particular strips 136 and strips 146 are overlapping. For example, a counter-clockwise rotation of the second plate 140 relative to the first plate 130 may cause the patterned conductive region 144 to shift slightly to the left away from the patterned conductive region 134, such that strip "g" overlaps with strips 11 and 12 (instead of strips 13 and 14 as shown in FIG. 3C), strip "f" overlaps with strips 9 and 10 (instead of strips 11 and 12), and so on with strip "a" ceasing to overlap with any of the strips 136. Accordingly, the capacitance signals from the first channel C1 and/or second channel C2 in the patterned conductive region 134 may change. The measurable change in relative position may, for example, be correlated to the change in capacitance signal $C_1$ from the channel C1 and/or capacitance signal $C_2$ from the channel C2 as shown in Equation 2 below:

$$\text{position} \sim \frac{C_1 - C_2}{C_1 + C_2} \quad (2)$$

Capacitance values (or changes in capacitance values) for each pair of facing patterned conductive regions on the first and second plates may be compared to determine direction and magnitude of relative in-plane motion.

Thus, in the capacitive sensor 100, the combination of signals from the non-patterned conductive regions and the patterned conductive regions may provide insight into relative movement of the first and second plates in up to six DOFs (X-direction, Y-direction, Z-direction, yaw, pitch, and/or roll). For example, in some variations, such as variations having first and second plates 130 and 140 shown in FIGS. 1 and 2, the capacitive sensor 100 may utilize at least nine capacitive sensing channels for measurement, including three channels for three non-patterned conductive regions, and six channels for three patterned conductive regions (two channels for each patterned conductive region). The number of measurement channels may increase or decrease with more or fewer conductive pads on the capacitor plates.

Furthermore, in some variations, the capacitive sensor 100 may include at least one reference conductive pad disposed on at least one of the first and second plates 130 and 140. For example, as shown in FIG. 1, the capacitive sensor 100 may include two reference conductive pads 138 located on or near the first surface (on or near the same surface as the non-patterned conductive regions 132a-132c and patterned conductive regions 134a-134c) on the first plate 130. The reference conductive pads 138 may be configured to provide at least one signal for calibrating the capacitive sensor 100 against environmental factors affecting capacitance signals, such as temperature and/or humidity.

In some variations, multiple reference conductive pads 138 may be distributed around the first surface on the first plate 130. In one example, the average capacitance signal from the reference conductive pads 138 may be used to calibrate all of the capacitance measurements from the measurement channels. In another example, the capacitance signals from each reference conductive pad 138 may be used only to calibrate capacitance measurements from nearby respective measurement channel or channels, so to provide more localized calibration. Such multiple reference conductive pads 138 may be unequally or equally distributed around the first plate 130 (e.g., two reference pads 138 disposed opposite or 180 degrees from one another, three reference pads 138 disposed at 120 degrees apart, etc.).

Alternatively, in some variations, at least one reference conductive pad 138 may be disposed in any suitable location (e.g., central to the first plate 130, or near a centroid of the conductive regions on the first plate 130) so as to provide a representative capacitance signal (either averaged from multiple reference conductive pads 138 placed closely together, or from a single reference conductive pad 138).

Accordingly, in some variations, such as variations having first and second plates 130 and 140 shown in FIGS. 1 and 2, the capacitive sensor 100 may utilize two additional capacitive sensing channels for calibration purposes, including one channel for each of two reference conductive pads 138. The number of calibration channels may increase or decrease with more or fewer reference conductive pads on the capacitor plates.

As shown in FIGS. 4A-4D, the capacitive sensor 100 may further include a base 110 configured to support the first and second plates 130 and 140. As shown in FIG. 4A, the base 110 may include at least a first base portion 112 and a second base portion 122, where the first and second base portions are rotationally displaceable, laterally displaceable, and/or axially displaceable relative to each other. The first and second base portions may be coupled to respective structures for which relative movement is to be characterized (e.g., links or joint modules of a robotic arm, as described in further detail below in an exemplary application). Generally, the first plurality of non-patterned conductive regions 132a-132c and the first plurality of patterned conductive regions 134a-134c may be fixed relative to the first base portion 112. The second plurality of non-patterned conductive regions 142a-142c and the second plurality of patterned conductive regions 144a-144c may be fixed relative to the second base portion 122. Accordingly, relative rotational movement, lateral movement, and/or axial movement between the first and second base portions may result in capacitive signal changes between facing non-patterned conductive regions, and between facing patterned conductive regions. These capacitive signal changes may be measured and interpreted in order to characterize the relative rotational movement, lateral movement, and/or axial movement in up to six DOF, as described above.

As shown in FIG. 4A, the first base portion 112 may include an outer rigid structure defining a central region within which the second base portion 122 is disposed. For example, the first base portion 112 may be ring-like, or generally cylindrical (e.g., as a single cylinder, a multi-segmented cylinder, etc.). As shown in FIG. 4B, the first base portion may include a surface 114 configured to receive the first plate 130. In some variations, the first plate 130 may be engaged with the surface 114, or otherwise coupled to the first base portion 112. For example, the surface 114 may include a cutout or recess that matches the shape of at least a portion of the first plate 130 to form a type of mechanical key, such that the first plate 130 is rotationally fixed relative to the first base portion 112. Additionally or alternatively, the first plate 130 may be coupled to the first base portion 112 via fasteners, epoxy, etc.

As shown in FIG. 4B, in some variations, the first base portion may include a first end 112a configured to couple to a first input structure (not pictured) whose movement relative to a second input structure (described below) is desired to be measured. For example, the first end 112a may be coupled to an input robotic arm link (or suitable mount connected thereto) via fasteners engaged with one or more holes 118. As shown in FIGS. 4B and 4C, a plurality of holes 118 may, for example, be arranged around a perimeter of the first end 112a in a generally radially symmetric manner, so as to couple the first base portion 112 to the first input structure in a generally evenly loaded manner. However, the holes 118 may be distributed in any suitable arrangement.

In some variations, as shown in FIG. 4B, the first base portion may include a second end 112b, such that a body of the first base portion extending between the first and second ends 112a and 122b defines a central region and substantially surrounds the second base portion 122 disposed in the central region. Furthermore, in some variations, the first base portion and second base portion may be configured to maintain a predetermined nominal gap between the first and second plates (e.g., the second base portion 122 may be separated in an axial direction from the first base portion 122). In some variations, the second end 112b may be coupled to the first structure (not pictured) along with the first end 112a. For example, securing the first base portion at two separate locations to the first input structure may ground the first base portion to the first input structure (and thereby bolster the overall rigidity of the coupled first base portion 112 and first input structure), such that the first plate 130 (and the conductive regions disposes on the first plate 130) moves more synchronously with movement of the first input structure.

As shown in FIGS. 4A-4D, the second base portion 122 may include a central structure that is disposed within the first base portion 112. The second base portion 122 is depicted as generally shaped as a rectangular block or rectangular prism in FIGS. 4-4D. However, in other variations, the second base portion 122 may include a cylinder, or a polygonal prism of any suitable cross-sectional shape, etc. As shown in FIG. 4B, the second base portion may include a surface 124 configured to receive the second plate 140 such that the conductive regions on the first and second plates 130 and 140 are facing each other. In some variations, the second plate 140 may be engaged with the surface 124, or otherwise coupled to the second base portion 122. For example, similar to the surface 114, the surface 124 may include a cutout or recess corresponding to the shape of at least a portion of the second plate 140 to form a type of mechanical key, such that the second plate 140 is rotationally fixed relative to the second base portion 122. Additionally or alternatively, the second plate 140 may be coupled to the second base portion 122 via fasteners, epoxy, etc.

As shown in FIGS. 4A and 4D, in some variations, the second base portion 122 may be configured to couple to a second input structure (not pictured) whose movement relative to the first input structure (described above) is desired to be measured. For example, the second base portion may be coupled to an input robotic arm link (or suitable mount connected thereto) via fasteners engaged with one or more holes 128. As shown in FIG. 4A, a plurality of holes 128 may, for example, be arranged around a perimeter of the second base portion 122 in a generally radially symmetric, so as to couple the second base portion 122 to the second input structure in a generally evenly loaded manner. However, the holes 128 may be distributed in any suitable arrangement.

As shown in FIGS. 4C and 4D, the second base portion 122 may be radially connected to the first base portion 112 through one or more cross-coupling members 126 that support relative rotational movement, lateral movement, and/or axial movement between the first base portion 112 and the second base portion 122. The members 126 may be, for example, cantilevered tab-like members that couple the second base portion 122 to the first base portion 112. FIG. 4C depicts an exemplary variation of a base 110 including four members 126 arranged on four sides of the second base portion 122. However, it should be understood that other variations of the base 110 may include fewer (e.g., one, two, or three) or more (e.g., five, six, seven, eight or more, etc.) cross-coupling members 126. In some variations, the members 126 may be distributed around the second base portion 122 in a radially symmetric manner, though they may be located in any suitable arrangement.

The members 126 may, in some variations, act as springs enabling the first base portion 112 and the second base portion 122 to move relative to one another in any of up to six DOFs. Varying degrees of stiffness (e.g., torsional stiffness, linear stiffness) of the base 110 in different directions may be achieved with different designs of members 126. Accordingly, in some variations, the first base portion 112 and the second base portion 122 may form a torsional spring and/or linear spring that is movable in up to six DOF. In some variations, the first base portion 112 and second base portion 122 may form a torsional spring and/or linear spring having a spring constant of at least about 5,000 rad/N-m, at least about 7,500 rad/N-m, at least about 10,000 radian/N-m, between about 5,000 rad/N-m and about 15,000 radian/N-m, between about 7,500 rad/N-m and about 12,500 rad/N-m, or about 10,000 rad/N-m. For example, in some variations, a sensor including a base with a torsional and linear spring constant of about 10,000 rad/N-m used in combination with suitably sensitive electronics may have a measurement sensitivity of generally up to about 10 nm of movement. In some variations, torsional spring constant may be similar to the linear spring constant. In some variations, the base may have a higher torsional spring constant and a lower linear spring constant (e.g., such that the sensor is less sensitive to torque measurements than, for example, force measurements). In other variations, the base may have a lower torsional spring constant and a higher linear spring constant (e.g., such that the sensor is more sensitive to torque measurements than, for example, torque measurements). The stiffness of the cross-coupling member or members 126 may be pre-determined and considered in interpreting the sensor readout resulting from the multi-directional relative movement between the first and second base portions (and between the plates) of the base 110.

Thus, as the first and second input structures move relative to one another in multiple DOF s, or up to six DOF (e.g., relative rotational displacement, relative axial displacement, etc.), so do the first and second base portions 112 and 122 (and plates 130 and 140). The facing non-patterned and patterned conductive regions on the plates 130 and 140 may accordingly provide capacitive signals that may be measured and interpreted to characterize the relative movement of the first and second input structures in up to six DOF, in the manner described above.

In some variations, as shown in FIG. 4B, the capacitive sensor 100 may further include a cover 150 configured to couple to the base 110 such that the cover and the base cooperatively substantially enclose the first and second plates 130 and 140. In some variations, the cover may be separately formed from the base 110 as shown in FIG. 4B and coupled to the base with fasteners, threads, etc. For example, as shown in FIG. 4B, the cover 150 may include a plate including one or more holes 152, and one or more fasteners 160 may pass through holes 152 and into a fastening feature of the base 110 such as into holes 118 on the first base portion 112. As another example, the cover 150 may include a cap with internal threads (or external threads) that threadingly mates with a portion of the base 110. As yet another example, the cover may couple to the base via a snap fit, a press fit (e.g., due to dimensional differences and/or interference features such as a ridge).

The base 110 and/or cover 150 may be made of a suitable rigid material. For example, the base 110 and/or cover 150 may be made of stainless steel, aluminum, or other suitable metal or rigid plastic. The base 110 and/or cover 150 may be machined, welded, injection molded, 3D printed, or made in any suitable manner.

Another exemplary variation of a multi-DOF capacitive sensor 500 is shown in FIGS. 5-8. As shown in FIGS. 5A and 5B, the capacitive sensor 500 may include a base 510 including a first base portion 512 and a second base portion 514. Additionally, as shown in FIG. 7, the capacitive sensor 500 may include a first plate 530 including a first plurality of non-patterned conductive regions 532a-532c and a first plurality of patterned conductive regions 534a-534c. As shown in FIG. 8, the capacitive sensor 500 may include a second plate 540 including a second plurality of non-patterned conductive regions 542a-542c and a second plurality of patterned conductive regions 544a-544c. Generally, the first and second plates 530 and 540, and their respective conductive regions, may be similar to the first and second plates 130 and 140 described above with reference to FIGS. 1 and 2, with similar elements labeled with like numbering. One of the plates may be an "active" or "sensor" plate, while the other plate may be a "ground" plate. The "active" plate may further include electronics for measuring capacitance between the first and second plates (although alternatively signals from the "active" conductive regions may be passed to electronics located in any suitable location, such as on the "ground" plate, the base 510 or other suitable housing).

Figure 6B:
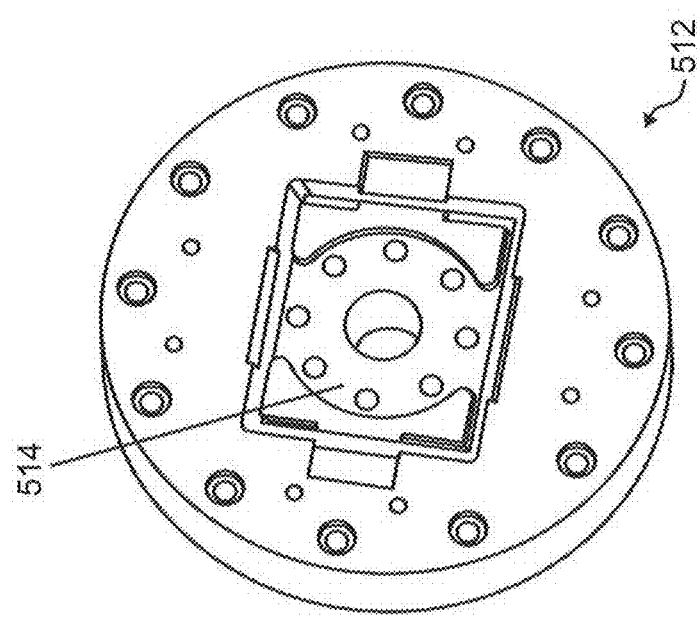
FIGS. 6A and 6B are top and bottom views, respectively, of a portion of the base in the sensor variation depicted in FIGS. 5A-5C.
Figure 6A:
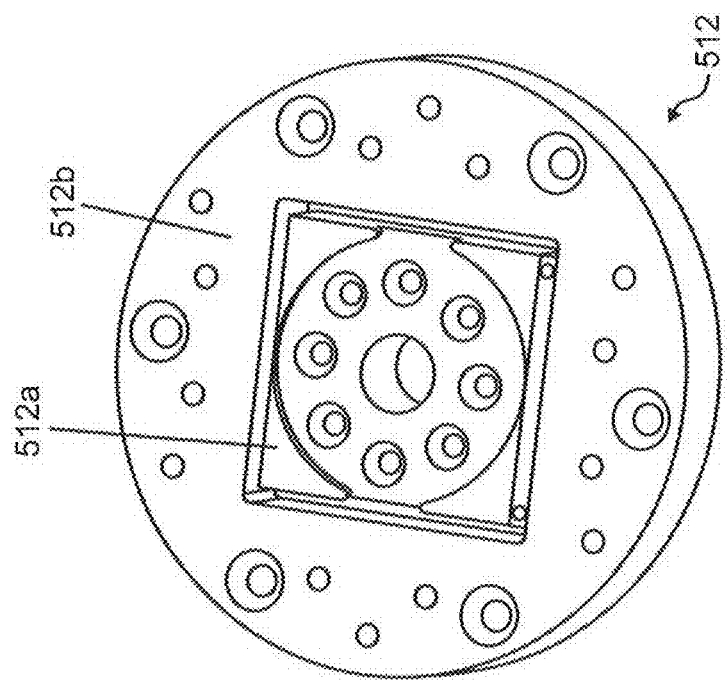

As shown in FIGS. 6A and 6B, the first base portion 512 may include an inner region 512a and an outer region 512b, where the inner region 512a and outer region 512b may be movable relative to each other (e.g., in rotation and/or translation in an in-plane direction and/or out-of-plane direction). For example, similar to the base 110 described above, the first and second base portions 512 and 522 may be coupled via one or more members, and may form a torsional spring and/or linear spring. The inner region 512a may be centrally located within the first base portion 512. In some variations, the inner region 512a may be coupled to a first input structure (e.g., a robotic link or a mount structure coupled thereto) with fasteners 526 passing through holes 528 in the inner region 512a. The second base portion 522 may similarly include an inner region 522a and an outer region 522b movable relative to each other similar to regions 512a and 512b. Additionally, in some variations, the inner region 522a may be coupled to a second input structure in a manner similar to that described above for the inner region 512a.

In some variations, the first and second base portions 512 and 522 may be identical or substantially identical (e.g., two instances of the same designed part or similarly designed parts). Although the base portions are depicted in FIGS. 6A and 6B as generally circular and with inner regions that are generally square, it should be understood that the base portions may be any suitable shape (e.g., square, rectangular, other suitable polygonal shape).

As shown in the exploded view of FIG. 5C, the first base portion 512 may include a surface 514 configured to receive a first plate 530. Similar to the capacitive sensor 100, the first base portion 512 may include a cutout or recess shaped to correspond with the shape of the first plate 530. Additionally or alternatively, one or more fasteners, epoxy, or other suitable mechanism may be used to couple the first plate 530 to the first base portion 512. The second base portion 522 may similarly include a surface 524 configured to receive a second plate 540.

The first base portion 512 and the second base portion 522 may be secured to each other to form a rigid base assembly that encloses the first and second plates 530 and 540. For example, as shown in FIG. 5A, with reference also to FIG. 5C, one or more fasteners 560 may couple the first base portion 512 and the second base portion 522 to each other. For example, a plurality of fasteners 560 passing through holes 562 may be arranged around the perimeter of the base portions, with radially symmetric distribution or any suitable arrangement. In some variations, a first portion (e.g., about half) of the fasteners 560 may approach from a first side of the base assembly such that their heads are in contact with the first base portion 512, while a second portion (e.g., about half) of the fasteners 560 may approach from a second side of the base assembly such that their heads are in contact with the second base portion 522. In these variations, the first and second portions of the fasteners 560 may alternate. Such an arrangement may, for example, contribute to a more balanced rigid base assembly. Furthermore, in variations in which the first base portion 512 and the second base portion 522 are identical, the base portions may be rotationally offset by a certain amount (e.g., 90 degrees) to accommodate an alternating pattern for the first and second portions of fasteners 560.

Accordingly, the base 510 may permit relative movement between the inner region 512a of the first base portion 512 and the inner region 522a of the second base portion 522, while the first and second base portions are rigidly fixed to one another. The inner region 512a may be coupled to the first plate 530 and a first input structure, and the inner region 522a may be coupled to the second plate 540 and a second input structure. Thus, as the first and second input structures move relative to one another in up to six DOF, so do the inner regions 512a and 522b (and plates 530 and 540). The facing non-patterned and patterned conductive regions on the plates 530 and 540 may accordingly provide capacitive signals that may be measured and interpreted to characterize the relative movement of the first and second input structures in up to six DOF, in the manner described above.

The base 510 may be made of a suitable rigid material. For example, the base 510 may be made of stainless steel, aluminum, or other suitable metal or rigid plastic. The base 510 may be machined, welded, injection molded, 3D printed, or made in any suitable manner.

Figure 9B:
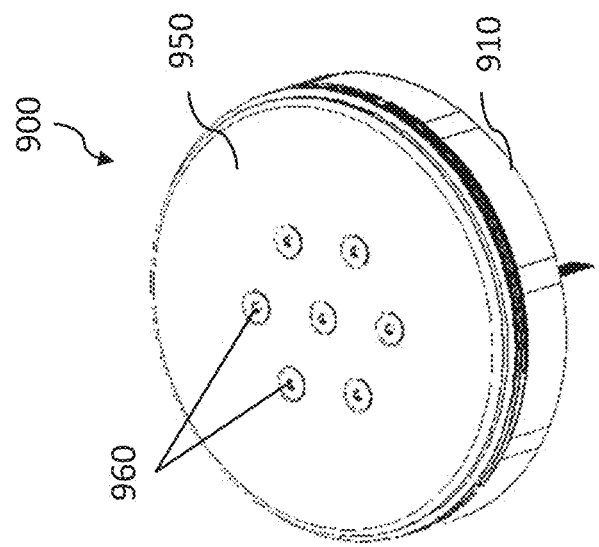
Figure 9A:
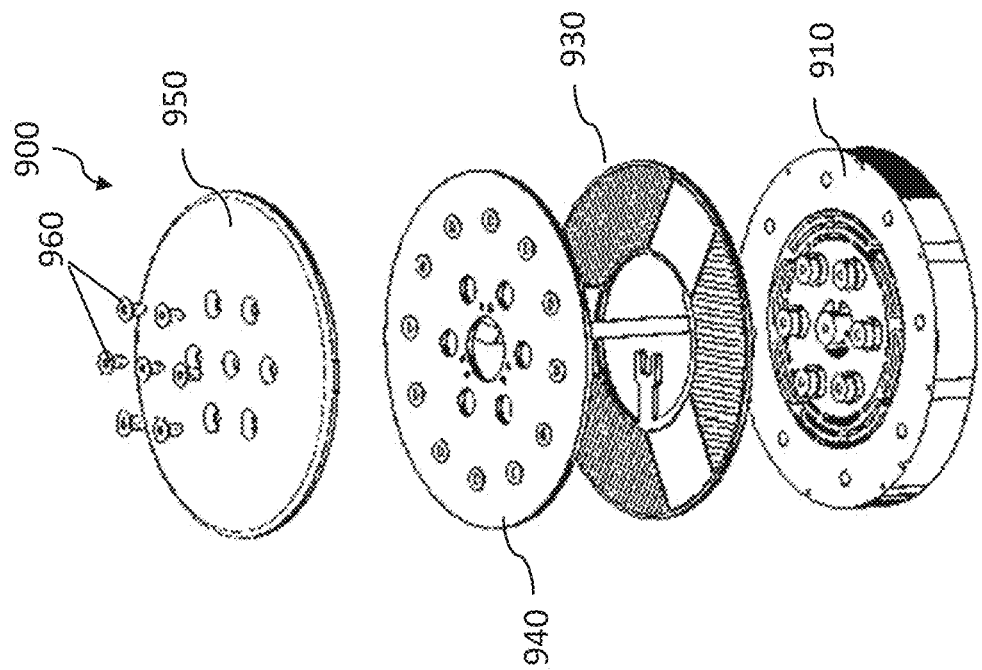

Another exemplary variation of a multi-DOF capacitive sensor 900 is shown in FIGS. 9A-9D. As shown in FIG. 9A, the capacitive sensor 900 may include a first plate 930 including a first plurality of non-patterned conductive regions (e.g., 932a, 932b, and 932c as shown in FIG. 9C) and a first plurality of patterned conductive regions (e.g., 934a, 934b, and 934c as shown in FIG. 9C) and a second plate 940 including a second plurality of non-patterned conductive regions (e.g., 942a, 942b, and 942c as shown in FIG. 9D) and a second plurality of patterned conductive regions (e.g., 944a, 944b, and 944c as shown in FIG. 9D). The first and second plates 930 and 940 may be generally axially aligned and spaced apart. The first and second plates may be supported by a base 910, as further described below.

Similar to the non-patterned conductive regions described above, in the variation shown in FIGS. 9A-9D a non-patterned conductive region (e.g., 932a-932c, 942a-942c) may cover or span a solid, substantially continuous capacitive surface area. In contrast, a patterned conductive region (e.g., 934a-934c, 944a-944c) may include a patterned mix of conductive and non-conductive surface area. For example, as shown in FIGS. 9C and 9D, a patterned conductive region may include a stripline pad with regularly alternating conductive strips and non-conductive strips. However, a patterned conductive region with other suitable patterns (e.g., checkered, alternating sine waves or other curved lines, polka dots, etc.) may be included in the first and/or second capacitor plates. In some variations, the pattern may be substantially regularly repeated across the surface area of the patterned conductive regions. In the patterned conductive regions, there may be common electrical ground pads that overlap each patterned conductive pad to form the non-capacitive regions of the patterned conductive pad.

FIG. 9C illustrates an exemplary arrangement of the first plate 3930 and its non-patterned and patterned conductive regions, while FIG. 9D illustrates an exemplary arrangement of the second plate 940 and its non-patterned and patterned conductive regions. The arrangements of conductive pads on the first and second plates may, in some variations, be generally similar (i.e., mirror one another) and/or may be generally radially symmetrical. As shown in FIGS. 9C and 9D, the first plate 930 and second plate 940 may be generally ring-shaped or circular, with non-patterned and patterned conductive regions shaped and arranged as ring segments around the center of the ring. For example, as shown in FIG. 9C, the first plate 930 may include three non-patterned conductive regions 932a, 932b, and 932c and three patterned conductive regions 934a, 934b, and 934c equally distributed around the plate 930 in alternating fashion. Similarly, as shown in FIG. 9D, the second plate 940 may include three non-patterned conductive regions 942a, 942b, and 942c and three patterned conductive regions 944a, 944b, and 944c equally distributed around the second plate 940 in alternating fashion. However, the number and size of patterned and non-patterned regions may vary. In some variations, at least some of the non-patterned conductive regions and patterned conductive regions are separate conductive pads.

Similar to the other capacitive sensor variations described above, the first and second plates may be arranged facing one another such that the non-patterned conductive regions on the first and second plates are generally facing, and the patterned conductive regions on the first and second plates are generally facing. For instance, as shown in FIGS. 9C and 9D, the non-patterned conductive regions 932a, 932b, and 932c on the first plate 930 may face and correspond to the non-patterned conductive regions 942a, 942b, and 942c on the second plate 940, respectively. Similarly, the patterned conductive regions 934a, 934b, and 934c on the first plate 930 may face and correspond to the patterned conductive regions 944a, 944b, and 944c on the second plate 940, respectively. As shown in FIG. 9H, one of the plates (e.g., the second plate 940) may be an "active" or "sensor" plate, while the other plate may be an electrical "ground" plate. The "active" plate may further include electronics 946 (shown in FIG. 9H) for measuring capacitance between the first and second plates (e.g., circuitry with voltage comparators, timers, etc. to measure decay of the output signal from the conductive regions, and thereby measure capacitance). For example, the electronics 946 may be located in a central region of the plate such that all of the conductive regions are similarly accessible via electrical traces or other suitable conductive connection. Alternatively, the electronics 946 may be distributed in any suitable manner on the plate. Furthermore, in other variations, the electronics may be located on the "ground" plate, the base 910, other suitable hosing, or other suitable location to receive the signals from the conductive regions on the "active" plate.

Similar to the capacitive sensor variations described above, the signals from the non-patterned conductive regions 932a-932c on the first plate 930 and/or the non-patterned conductive regions 942a-942c on the second plate 940 may be sensitive to gap size variations between the first plate 930 and the second plate 940. Accordingly, the capacitive sensor 900 may determine relative axial movement (e.g., in a Z-direction) and/or out-of-plane rotation (e.g., yaw or pitch) between the first and second plates based at least partially on detected or measured gap distance between at least one of the non-patterned conductive regions 932a-932c and at least one of the non-patterned conductive regions 942a-942c.

Furthermore, also similar to the capacitive sensor variations described above, the signals from the patterned conductive regions 934a-934c on the first plate 930 and/or the patterned conductive regions 944a-944c on the second plate 940 may be sensitive to detecting relative in-plane motion of the first and second plates. For example, the capacitive sensor 900 may determine relative lateral movement (e.g., in an orthogonal X-direction and/or Y-direction, or rotation in a roll direction) between the first plate 930 and the second plate 940 based at least partially on the detected area of the patterned regions 934a-934c on the first plate 930 that overlap with the patterned regions 944a-944c on the second plate 940 (e.g., overlapping stripline regions 934a and 944a as shown in FIG. 9I).

As described in further detail above, each pair of facing patterned regions may provide an output signal value that is proportional to the overlapping area between the pair of facing patterned regions. The ratios of values for each pair of patterned regions can indicate direction of axial misalignment, rotational displacement, etc. between the plates. Alternatively, the capacitive sensor may determine relative translation and/or relative rotation through a patterned pad capacitor model (e.g., strip line pads capacitor model), instead utilizing differential measurements of overlap area on the pattered conductive regions.

As shown in FIG. 9E, the capacitive sensor 900 may include a base 910 configured to support the first plate 930 and the second plate 940. For example, as shown in FIG. 9E, the base 910 may include a first base portion 912 and a second base portion 922 that are movable relative to one another in up to six DOF. The first base portion 912 may, for example, include an outer region (e.g., ring-shaped), and the second base portion 922 may include a central region that is radially connected to the first base region 912 via one or more cross-coupling members 926. The first plate 930 may be coupled to the first base portion 912 of the base 910, while the second plate 940 may be coupled to the second base portion 922 of the base 910, or vice versa, such that relative movement between the first and second base portions causes corresponding relative movement between the first and second plates (and their respective conductive regions). In some variations, the second base portion 922 may be slightly thicker than the first base portion 912, or vice versa, such that the first and second plates, when resting on and secured to the outer region 312 and central region 316, are separated by a predetermined default gap distance between the first and second plates (e.g., between about 100 μm and about 500 μm, or around 200 μm). Additionally or alternatively, the sensor assembly may include a riser or other spacer to establish a default gap distance between the plates.

The members 926 in the base 910 may act as springs, thereby enabling the first base portion 912 and the second base portion 922 to function as a torsional spring and/or linear spring movable in up to six DOF. Varying degrees of stiffness (e.g., torsional stiffness, linear stiffness) of the base 910 in different directions may be achieved with different designs of members 926. For instance, in the example shown in FIG. 9E, the members 926 include an arcuate loop with radial extensions connecting the first base portion 912 and the second base portion 922. In the example shown in FIG. 9F, the member 926' is a ring encircling the second base portion 922', with extensions connecting the member 926' to the first base portion 912' and the second base portion 922'. The stiffness of the cross-coupling member or members 926 may be pre-determined and considered in interpreting the sensor readout resulting from the multi-directional relative movement between the first and second base portions (and between the plates) of the base 910. In some variations, the base 910 may include materials, spring constants, etc. similar to the other base variations described herein.

Similar to the capacitive sensor variations described above, the first and second base portions may be coupled to first and second input structures (e.g., robotic arm links, etc.), respectively. Thus, as the first and second input structures move relative to one another in up to six DOF (e.g., relative rotational displacement, relative axial displacement, etc.), so do the first and second base portions 912 and 922 (and plates 930 and 940). The facing non-patterned and patterned conductive regions on the plates 930 and 940 may accordingly provide capacitive signals that may be measured and interpreted to characterize the relative movement of the first and second input structures in up to six DOF.

Figure 9G:
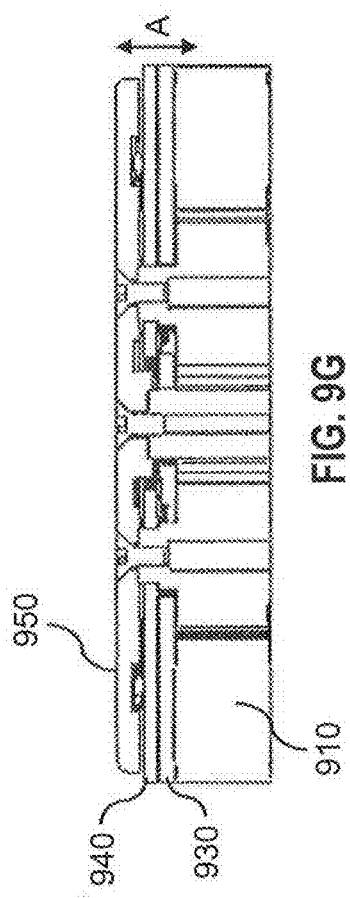
Figure 9I:
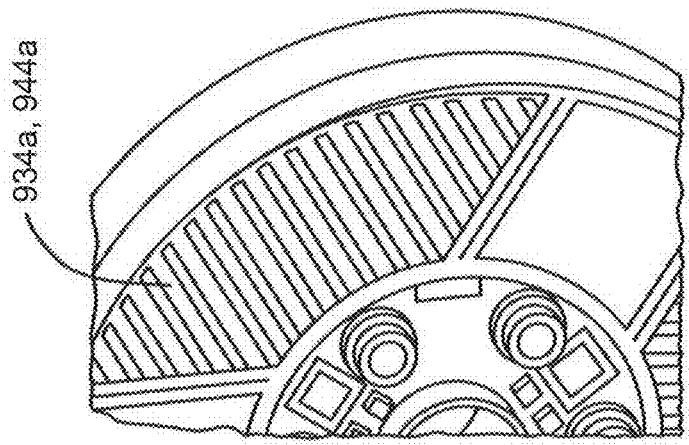
Figure 9H:
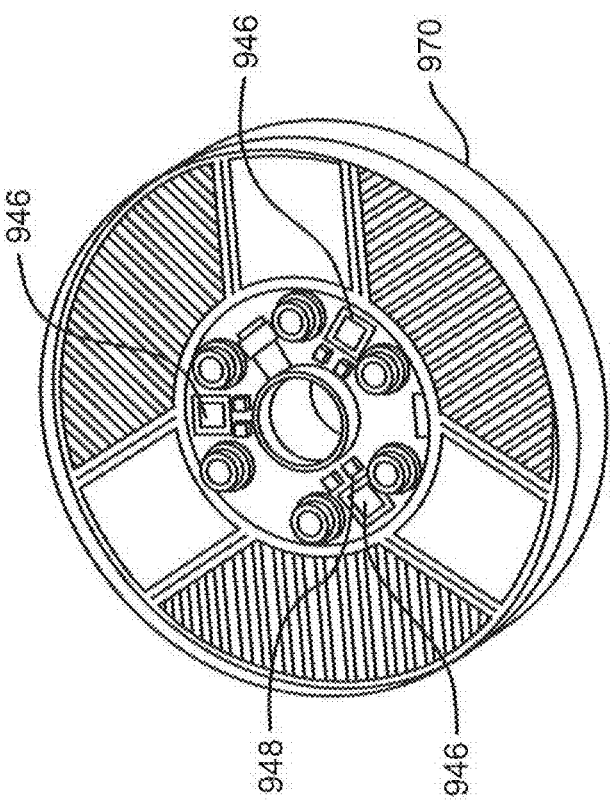

As shown in FIGS. 9A and 9G, the capacitive sensor may further include a cover 950 may configured to couple to the base 910 to enclose the first and second plates. Fasteners 960 (e.g., screws) may secure the cover 950 to the base 910.

Additionally or alternatively, the cover 950 may couple to the base 910 via threads, interference fit, epoxy, or in any suitable manner.

In any of the variations described herein, the multi-DOF capacitive sensor may include an alarm element configured to trigger a remedial action in the event there is physical contact between the first and second capacitor plates (which may, for example, indicate an interference or overdrive event, etc. has occurred), so as to avoid damage to the capacitive sensor and/or other components of a system incorporating the capacitive sensor. For example, as shown in FIG. 9H, upon measuring a capacitance indicating contact between any of the conductive regions (or receiving a signal from a contact or pressure sensor disposed on one of the plates, etc.), an LED 948 may be activated to visually indicate an error and trigger a remedial action. Additionally or alternatively, the capacitive sensor may send a signal indicating the contact event to a control system (e.g., a control system operating a robotic arm, such as that described below), whereupon the control system may take remedial action. For example, suitable remedial actions may include providing a notification to the user (audio and/or visual alarm, vibrational alert to a handheld control device that is controlling a system incorporating the multi-DOF capacitive sensor, etc.) indicating the contact event, commanding actuation of the input structures in a reverse direction, halting actuation of the input structures, etc.

Furthermore, in any of the variations described herein, the capacitive sensor may include a seal to help exclude dirt and other debris from entering the capacitive sensor (e.g., between the conductive regions), and/or to maintain humidity levels and other environmental conditions which could interfere with the accuracy of the capacitive sensor readings. For example, as shown in FIG. 9H, the capacitive sensor may include a seal 970 circumferentially around the interface between the base 910 and cover 950. The seal may include, for instance, a silicone or other rubber ring extending circumferentially around the edge of the base and cover, epoxy, etc.

EXAMPLE

Robotic Arm with Multi-DOF Capacitive Sensor

Described below is an exemplary use of a multi-DOF capacitive sensor in a system. Although the figures and description refer to inclusion of a multi-DOF capacitive sensor in a robotic arm (e.g., for robotic surgery), it should be understood that in other applications, a multi-DOF capacitive sensor may be incorporated in any suitable kind of robotic system or other suitable system.

Robotic Arm-Overview

Generally, a robotic or robotic-assisted surgical system (e.g., to enable a minimally-invasive surgical procedure) may include one or more robotic arms for manipulating surgical instruments, such as during minimally-invasive surgery. A robotic arm may include a plurality of links, a plurality of actuated joint modules that enable relative movement between adjacent links. For example, as shown in FIG. 10A, a robotic arm may include a first segment 1010 having a proximal end and a distal end, and a second segment 1050 having a proximal end (coupled to the distal end of first segment 1010) and a distal end. Additionally, an instrument driver 1080 may be coupled to the distal end of second segment 1050 and be configured to hold and actuate a surgical instrument passing through a cannula 1090. An exemplary robotic surgical system is described in U.S. patent application Ser. No. 15/706,536 filed concurrently herewith and titled "ROBOTIC ARMS", which is hereby incorporated in its entirety by this reference.

During use of the robotic arm 1000 for a surgical procedure, the proximal end of first segment 1010 may be mounted or otherwise coupled to a structure (e.g., a surgical table, cart, wall, ceiling, etc.) at a mounting point near the patient during a surgical procedure. In some variations, the first segment 1010 may be referred to as the "Cartesian arm" segment because the first segment 1010 may position a mechanical remote center of motion (further described below) in three-dimensional space (e.g., x-y-z coordinates) relative to the mounting point of the first segment 1010. Furthermore, the second segment 1050 may be referred to as the "spherical arm" segment because the second segment 1050 may move the tip of the surgical instrument held by the instrument driver within an approximately spherical volume of space as defined by the range of motion of the second segment 1050. The combination of the Cartesian arm segment and the spherical arm segment may provide for a high degree of setup flexibility and dexterity for manipulating the surgical instrument for various procedure types and patient types.

Multi-DOF Capacitive Sensor Mount

In some variations, a robotic arm may include at least one multi-DOF capacitive sensor for characterizing force and/or torque applied to the arm. For example, the capacitive sensor may characterize up to six DOFs (three directions of force and three directions of torques) by measuring small displacements between two adjacent links, including translation along an X-axis, translation along a Y-axis, translation along a Z-axis, rotation around a roll axis, rotation around a pitch axis, and rotation around a yaw axis.

As shown in FIGS. 16A and 16B and further described below, in one embodiment, a multi-DOF capacitive sensor may be disposed between the first and second arm segments (e.g., between a joint module 1634*e* and a joint module 1634*f*). In this embodiment, the capacitive sensor may be configured to provide signals measuring and otherwise characterizing force and/or torque that is multi-directionally applied to the robotic arm on the second segment (spherical arm). Additionally or alternatively, the capacitive sensor may be configured to measure force and/or torque in other locations of a robotic arm. For example, the capacitive sensor may include a base with higher torsional stiffness than linear stiffness, which may make the capacitive sensor suitable for measuring primarily force in up to 3 DOF. Such a capacitive sensor may, for example, be placed near a proximal base of the robotic arm (e.g., near base link 1012, or between base link 1012 and shoulder pitch link 1014, etc. described further below). Other suitable locations include between any adjacent joints or links in the robotic arm.

The signals from the capacitive sensor characterizing the force and/or torque may, for example, be used as inputs for the control algorithm when the control system is operating in admittance control mode (described further below). For instance, as described in further detail below, at least some of the force and/or torque measurements provided by a multi-DOF capacitive sensor may serve as inputs for a control system of the robotic arm. For example, the force and/or torque measurements may be inputs into a virtual model of the robotic arm, where the response of the virtual model to the force/torque inputs forms the basis of the actuator commands for the robotic arm.

FIGS. 16A-16D illustrate an exemplary assembly including at least a portion of a robotic arm and a multi-DOF capacitive sensor. Although these figures depict a multi- DOF capacitive sensor similar to that described above, it should be understood that other variations of a multi-DOF capacitive sensor may similarly be mounted and assembled with a portion of a robotic arm.

Figure 16D:
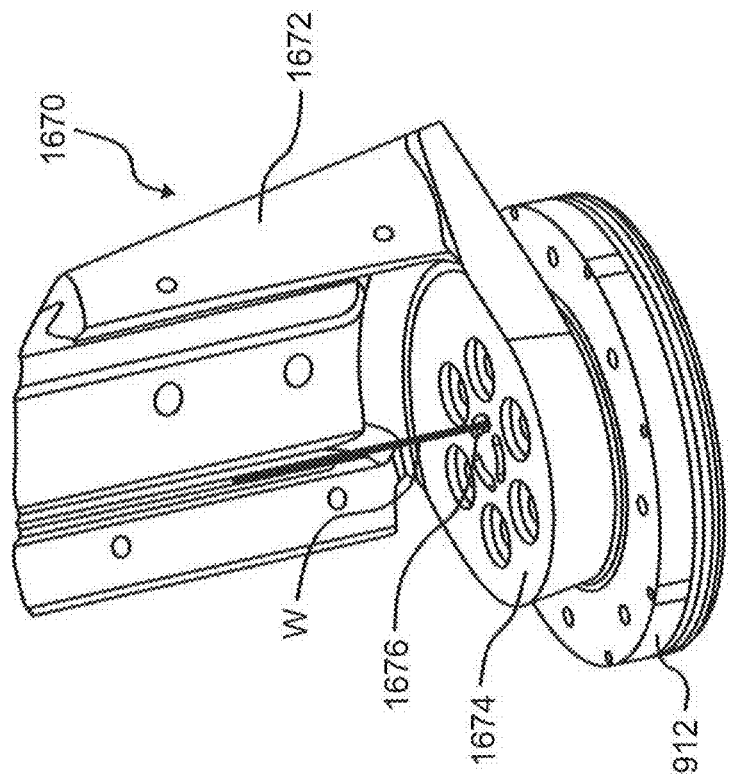
FIGS. 16C and 16D are a perspective view of a first sensor mount portion coupled to part of a multi-DOF capacitive sensor, and a perspective view of a second mount portion coupled to part of the multi-DOF capacitive sensor.

As shown in FIGS. 16A and 16B, a multi-DOF capacitive sensor (e.g., for exemplary illustrative purposes, capacitive sensor 900 as described above) may be located between a joint module 1634e and a joint module 1634f in a robotic arm, though the capacitive sensor or other instances and/or variations of the capacitive sensor may additionally or alternatively be incorporated elsewhere in the robotic arm. An exemplary mounting setup for the capacitive sensor 900 is shown in greater detail in FIGS. 16B-16D. As shown in FIG. 16B, a sensor mount 1650 may be located generally between the joint module 1634e and the joint module 1634f. In some variations, the sensor mount 1650 may include a first mount portion 1660 and a second mount portion 1670. Generally, the first mount portion 1660 may be configured to couple to the joint module 1634e and one of the first and second base portions 912 and 922 of the capacitive sensor 900. Similarly, the second mount portion 1670 may be configured to couple to the joint module 1634f and the other of the first and second base portions 912 and 922. Accordingly, the first mount portion 1660 and second mount portion 1670 may functions as input structures communicating to the capacitive sensor 900 force and/or torque imparted on the joint modules 1634e and 1634f.

Figure 16C:
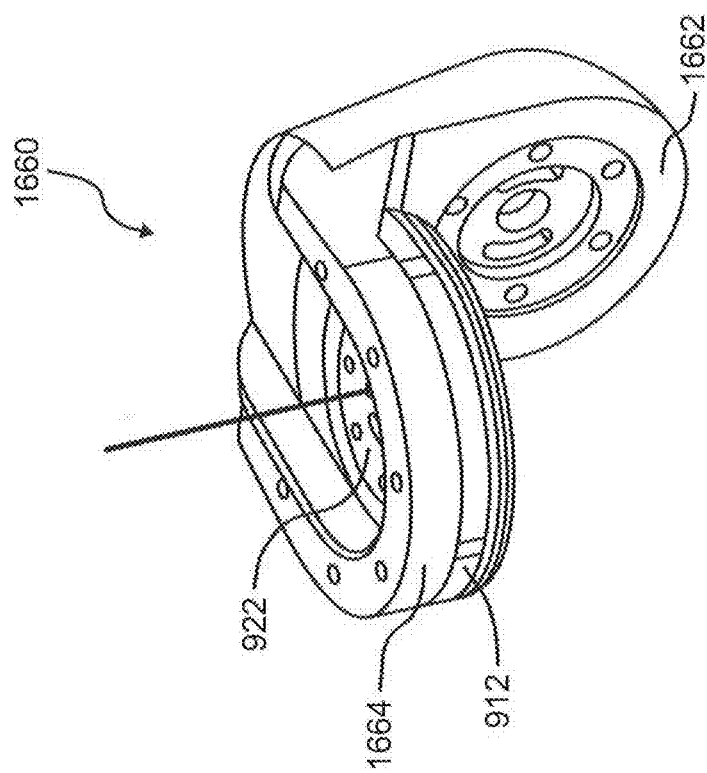

For example, as shown in further detail in FIG. 16C, the first mount portion 1660 may include a joint module mount 1662 configured to couple to the joint module 1634e. The joint module mount 1662 may, for example, couple to the joint module 1634e via fasteners, interference fit, epoxy, threads, and/or or any suitable attachment arrangement. The first mount portion 1660 may further include a sensor mount 1664 configured to couple to the first base portion 912 of the capacitive sensor 900. The sensor mount 1664 depicted in FIG. 16C may, for example, include a generally arcuate (e.g., horseshoe-shaped) member to correspond to at least part of the outer ring shape of the first base portion 912. The sensor mount 1664 may include one or more holes that may be aligned with corresponding holes in the first base portion 912, such that one or more fasteners (e.g., screws or pins) may pass through the aligned holes to couple the first base portion 912 of the capacitive sensor 900 to the sensor mount 1664. However, it should be understood that in other variations, the joint module mount 1662 and the sensor mount 1664 may be shaped in any suitable manner and/or may couple to the joint module 1634e and the first base portion 912, respectively, in any suitable manner.

As shown in further detail in FIG. 16D, the second mount portion 1670 may include a joint module mount 1672 configured to couple to the joint module 1634f, such as with fasteners, interference fit, epoxy, threads, and/or any suitable attachment arrangement. The second mount portion 1670 may further include a sensor mount 1674 configured to couple to the second base portion 922 of the capacitive sensor 900. The sensor mount 1674 depicted in FIG. 16D may include an extension 1674 that is generally circular and corresponding to at least part of the circular-shaped second base portion 922. Like the sensor mount 1664, the sensor mount 1674 may include one or more holes that may be aligned with corresponding holes in the second base portion 922, such that one or more fasteners may pass through the aligned holes to couple the second base portion 922 of the capacitive sensor 900 to the sensor mount 1674. However, it should be understood that in other variations, the joint module mount 1672 and the sensor mount 1674 may be shaped in any suitable manner and/or may couple to the joint module 1634f and first base portion 912, respectively, in any suitable manner.

Alternatively, the first mount portion 1660 may couple to the second base portion 922 of the capacitive sensor 900 and the second mount portion 1670 may couple to the first base portion 912 of the capacitive sensor 900. One or both of the mount portions 1660 and 1670 may further include holes or other suitable channels for passing sensor wires (for communication, power, etc.) to and from the capacitive sensor 900. For example, as shown in FIG. 16D, at least one sensor wire W may pass to and from electronics in the capacitive sensor 900 through a hole 1676 in the sensor mount 1674.

Thus, in this above-described application of a multi-DOF capacitive sensor in a robotic arm, multi-directional forces and/or torques applied to the second segment (spherical arm) of the robotic arm may in relative motion between the first mount portion 1660 (corresponding to the first base portion 912 of the capacitive sensor) and the second mount portion 1670 (corresponding to the second base portion 922 of the capacitive sensor). Accordingly, the forces and/or torques, as reflected in the relative movement in up to six DOF between the first and second base portions 912 and 922 of the capacitive sensor, may be measured by the capacitive sensor 900 via interpretation of capacitive signals from the conductive regions in plates coupled to the first and second base portions 912 and 922. Other multi-DOF capacitive sensors may be placed in other suitable locations in the robotic arm to measure forces and/or torques at those locations.

Signals from the capacitive sensor may be passed via wires (or alternatively, wirelessly through a suitable wireless communication protocol) to one or more processors and/or one or more suitable storage devices. For example, capacitive measurement signals from the capacitive sensor may be passed to one or more processors of a control system (e.g., described below) to function as inputs to one or more control algorithms. As another example, capacitive measurement signals may additionally or alternatively be stored in a memory device (e.g., flash memory, hard drive, portable storage device). Capacitive measurement signals may be stored, for example, for use in a control algorithm, for recording of forces and/or torques experienced during research and development, testing, calibration, characterization of surgical procedures or tasks, etc. It should be understood that in other variations, measurement of forces and/or torques in up to 6 DOF may be used in any suitable application.

Robotic Arm Links

As described above, a robotic arm may, in some variations, include a first segment 1010 and a second segment 1050. For example, as shown in the variation depicted in FIG. 10B, the first segment 1010 may include a first plurality of links and a first plurality of actuated joint modules for actuating the first plurality of links relative to one another. For example, the first segment 1010 may include at least five links: a base link 1012, a shoulder pitch link 1014, a shoulder roll link 1016, an elbow link 1018, and a forearm link 1020, which are arranged in series. Adjacent links may be connected in a manner such that the adjacent links are substantially constrained to movement around one axis relative to one another. For example, the base link 1012 and the shoulder pitch link 1014 may be substantially constrained to relative movement around a pitch axis (e.g., the angle between the longitudinal axis of the base link 1012 and the longitudinal axis of the shoulder pitch link 1014 may increase or decrease), such as with a clevis joint construction. The shoulder pitch link 1014 and the shoulder roll link 1016 may be substantially constrained to relative movement around a roll axis (e.g., the longitudinal axes of the shoulder pitch link 1014 and the shoulder roll link 1016 may be substantially coaxial). The shoulder roll link 1016 and the elbow link 1018 may be substantially constrained to relative movement around another pitch axis (e.g., the angle between the longitudinal axis of the shoulder roll link 1016 and the longitudinal axis of the elbow link 1018 may increase or decrease), such as by a clevis joint construction. The elbow link 1018 and the forearm link 1020 may be substantially constrained to relative movement around another roll axis (e.g., the longitudinal axes of the elbow link 1018 and the forearm link 1020 may be substantially coaxial).

Additionally, the first segment 1010 may include a first plurality of actuated joint modules 1032 configured to actuate the first segment 1010 with at least five degrees of freedom (DOFs), including at least two redundant DOFs beyond the 3 DOF task of positioning the mechanical remote center of motion in three-dimensional space. For example, with reference to FIGS. 10B, 10E, and 10F, a first joint module 1034a may couple the shoulder pitch link 1014 to the base link 1012, and include at least one actuator configured to pivot the shoulder pitch link 1014 around Axis A relative to the base link 1012. A second joint module 1034b may couple the shoulder roll link 1016 to the shoulder pitch link 1014, and include at least one actuator configured to rotate the shoulder roll link 1016 around Axis B relative to the shoulder pitch link 1014. A third joint module 1034c may couple the elbow link 1018 to the shoulder roll link 1016, and include at least one actuator configured to pivot the elbow link 1018 around Axis C relative to shoulder roll link 1016. A fourth joint module 1034d may couple the forearm link 1020 to the elbow link 1018, and include at least one actuator configured to rotate the forearm link 1020 around Axis D relative to the elbow link 1018. A fifth joint module 1034e may couple the second segment of the robotic arm (e.g., via spherical base link 1052) to the distal end of the first segment (e.g., forearm link 1020), and include at least one actuator configured to pivot the second segment of the robotic arm around Axis E relative to the forearm link 1020. Exemplary actuation and control schemes of the links are described in further detail below.

In some variations, at least some of the longitudinal axes of the first segment 1010 may be offset from the joints between adjacent links. For example, with reference to FIG. 10B, the longitudinal axis of the shoulder roll link 1016 and/or the longitudinal axis of the elbow link 1018 may be laterally offset from the center of the joint (e.g., elbow joint) actuated by joint module 1034c. This lateral offset may, for example, enable the shoulder roll link 1016 and the elbow link 1018 to fold against each other more compactly. A suitable lateral offset may be, for example, a distance to about a quarter of the diameter (or about half the radius) of the link. Similarly, lateral offsets of other links in the robotic arm relative to adjacent joint(s) may be included to further enable a compact, folded configuration of the robotic arm.

The second segment 1050 may include a second plurality of links and a second plurality of actuated joint modules for actuating the second plurality of links relative to one another. For example, as shown in FIG. 10B, the second segment 1050 may include at least four links: a spherical base link 1052, a spherical roll link 1054, and first and second pitch links 1056a and 1056b, respectively (shown in FIGS. 10C and 10D), forming spherical pitch assembly 1056. As described above, the spherical base link 1052 may be coupled to a distal end of the first segment (e.g., forearm link 1020) to connect the first arm segment 1010 and the second arm segment 1050. As in the first segment 1010, adjacent links in the second segment 1050 may be connected in a manner such that adjacent links are substantially constrained to movement around one axis relative to one another. For instance, with reference to FIGS. 10B, 10E, and 10F, the spherical base link 1052 may couple to the forearm link 1020 with a clevis joint construction that allows relative movement only around Axis E. Additionally, the spherical base link 1052 and the spherical roll link 1054 may be substantially constrained to relative movement around a roll axis (e.g., the longitudinal axes of the spherical base link 1052 and the spherical roll link 1054 may be substantially coaxial).

Additionally, the second segment 1050 may include a second plurality of actuated joint modules configured to provide the second segment 1050 with at least two DOFs. For instance, as shown in FIG. 10E, a sixth joint module 1034f may couple the spherical roll link 1054 to the spherical base link 1052, and include at least one actuator configured to rotate the spherical roll link 1054 around roll Axis F relative to the spherical base link 1052. In some variations, a 6-DOF capacitive sensor (e.g., as described herein, or other suitable variation) may be located between the fifth joint module 1034e and the sixth joint module 1034f For example, with reference to FIGS. 16A and 16B, the first mount portion 1660 may couple to the fifth joint module 1034e, and the second mount portion 1670 may couple to the sixth joint module 1034f.

A seventh joint module 1034g may couple the spherical pitch assembly (via first pitch link 1056a) to the spherical roll link 1054, and include at least one actuator configured to pivot the first pitch link 1056 around Axis G relative to the spherical roll link 1054. Exemplary actuation and control schemes of the links are described in further detail below.

As shown in FIG. 10G, the second segment 1050 may include a spherical pitch assembly 1056 including a first pitch link 1056a and a second pitch link 1056b. Instrument driver 1080 may be coupled to a distal end of second pitch link 1056b. For instance, as shown in FIG. 10H, the first pitch link 1056a, the second pitch link 1056b, and the instrument driver 1080 may move as three links of a parallelogram or four-bar linkage, constrained with a drive mechanism (such as that further described below) with 1:1 ratio in order to replicate the rotation of first pitch link 1056a around Axis G into rotation of the instrument driver around Axis G' at the mechanical remote center of motion (RCM), where pitch Axis G' is offset and parallel to Axis G. In other words, the seventh joint module 1034g may actuate the first pitch link 1056a to pivot around Axis G, which through the spherical pitch assembly 1056 indirectly actuates the instrument driver (and the surgical instrument held by the instrument driver) to pivot around Axis G' at the RCM. The pitch assembly 1056 may be configured to operate the surgical instrument about the RCM with increased ease, speed, and flexibility compared to other conventional pitch assembly mechanisms.

In some variations, with reference to FIG. 10C and 10D, the second segment 1050 may include a spherical roll link 1054 including a proximal portion 1054a and a distal portion 1054b coupled to the proximal portion 1054a. The proximal and distal portions 1054a and 1054b of the spherical roll link 1054 may, for example, be generally cylindrical and aligned along respective longitudinal axes. The proximal and distal portions 1054a and 1054b may have similar diameters. However, in other variations the proximal and distal portions 1054a and 1054b may have any suitable shape (e.g., prismatic, irregular, etc.). The proximal portion 1054a and the distal portion 1054*b* may be integrally formed (e.g., through injection molding, machining from a common piece, etc.) or may separately formed and coupled to one another (e.g., via fasteners, welding, or other joining). A bridge portion or the connecting feature may facilitate translational and/or angular offsets between the proximal and distal portions 1054*a* and 1054*b*, as described below.

The proximal portion 1054*a* may be oriented along a roll axis of the spherical roll link 1054, such that rotation of the proximal portion 1054*a* relative to the spherical base link 1052 provides motion of the instrument driver 1080 around a spherical roll axis (e.g., Axis F as shown in FIG. 10E). The distal portion 1054*b* of the spherical roll link 1054 may be oriented along a remote angled axis (e.g., Axis G shown in FIG. 10E) that is correlated to a pitch axis (e.g., Axis G'), where the angled axis is in a different plane than the spherical roll axis. For example, the remote angled axis may be an axis around which a parallelogram (formed at least in part by the first and second pitch links 556*a* and 556*b*) moves. In the robotic arm pictured in FIGS. 10B-10D, the distal portion 1054*b* (and its remote angled axis) is neither orthogonal nor parallel to the proximal portion 1054*a* (and its spherical roll axis).

In some variations, the proximal portion 1054*a* and the distal portion 1054*b* of the spherical roll link may be offset in one or more directions (e.g., at least two directions). For example, the distal portion 1054*b* may be translationally offset in a first direction from the proximal portion 1054*a* (e.g., as shown in the side view perspective shown in FIG. 10B). The translational offset in the first direction (e.g., as measured between the longitudinal axes of the proximal portion 1054*a* and the distal portion 1054*b*) may be, for example, between about 1 and about 2 times the diameter of the proximal portion 1054*a* or the distal portion 1054*b*, between about 1 and about 1.75 times the diameter of the proximal portion 1054*a* or the distal portion 1054*b*, or between about 1 and about 1.5 times the diameter of the proximal portion 1054*a* or the distal portion 1054*b*.

Additionally or alternatively, the distal portion 1054*b* may be angularly offset in a second direction from the proximal portion 1054*a* (e.g., as shown in the top view perspective shown in FIG. 10C and the front view perspective shown in FIG. 10D). For example, the angular offset between the longitudinal axis of the proximal portion 1054*a* (e.g., spherical roll axis) and the longitudinal axis of the distal portion 1054*b* (e.g., remote angled axis) may be an obtuse angle. As measured from a top view perspective (e.g., as shown in FIG. 10C), the angular offset in the proximal and distal portions of the spherical roll link may be, for example, between about 90 degrees and about 135 degrees, between about 90 degrees and about 125 degrees, or between about 90 degrees and about 105 degrees, etc. As measured from a front view perspective (e.g., as shown in FIG. 10D), the angular offset in the proximal and distal portions of the spherical roll link may be, for example, between about 90 degrees and about 135 degrees, between about 90 degrees and about 125 degrees, or between about 90 and about 105 degrees, etc. Accordingly, in the robotic arm pictured in FIGS. 10B-10D, the non-orthogonality of the spherical roll axis and the remote angled axis of the distal portion 1054*b* is achieved by translationally offset and angularly offset portions of the spherical roll link.

Alternatively, in some variations, the spherical roll link 1054 itself may be oriented only along a spherical roll axis. In these variations, the first pitch link 1056*a* may include a lateral angled projection coupled to the spherical roll link 1054 in order to achieve its rotation around an angled remote axis. Additionally or alternatively in these variations, the first pitch link 1056*a* may be coupled to the spherical roll link 1054 via any suitable angled coupling (e.g., directly to a portion similar to proximal portion 1054*a* of the spherical roll link). Accordingly, in these variations, the non-orthogonality of the spherical roll axis and the remote angled axis may be achieved by translationally offset and angularly offset coupled portions of the spherical roll link 1054 and the first pitch link 1056*a*.

In some variations, the first pitch link 1056*a* may be rotatable within a first plane, and the second pitch link 1056*b* may be rotatable within a second plane. For example, the first and second planes may be generally offset and parallel to one another. The instrument driver 1080 may be coupled to a distal end of the second pitch link 1056*b* such that the instrument driver is not parallel to at least one of the first and second planes (e.g., offset from a parallelogram formed at least in part by the first and second pitch links) and/or not parallel to at least a portion of the spherical roll link 554 (e.g., offset from the spherical roll axis).

One effect of non-orthogonality of the spherical roll axis (e.g., of at least the proximal portion 1054*a* of the spherical roll link) and the remote angled axis (e.g., of the distal portion 1054*b* of the spherical roll link) is that at least a portion of the pitch assembly may be angled relative to at least a portion of the spherical roll link 1054 (e.g., a parallelogram formed at least in part by the first and second pitch links may be angularly offset from the roll axis). Accordingly, space between the pitch assembly and the spherical roll link 1054 may be provided to enable another portion of the robotic arm and instrument assembly to nestle and further collapse into a more compact space. For example, as shown in FIGS. 10B-10D, at least the second segment 1050 of the robotic arm 1000 may be foldable into a compact configuration in which the instrument driver 1080 is positioned between the spherical roll link 1054 and at least one of the pitch links 1056*a* and 1056*b*, such as when the pitch links 1056*a* and 1056*b* are folded against each other and against the spherical roll link 1054. Accordingly, the second segment 1050 of the robotic arm may have a greater range of motion throughout folded and unfolded configurations made possible without physical interference between adjacent links, thereby providing for greater dexterity. Additionally, the offset nature of the spherical roll link, the pitch assembly, and the instrument driver may increase the robotic arm's general ability to fold into smaller volume, such as for storage and/or transport purposes.

In some variations, the pitch assembly 1056 may include first and second pitch links that are different lengths, where length is measured between pivoting points on the ends of a pitch link. For example, as shown in FIG. 10G, the first pitch link 1056*a* may be shorter than the second pitch link 1056*b*. For example, in some variations, the first pitch link 156*a* may have a length (as measured between pivot points) that is between about 10% and about 80% of the length of the second pitch link 156*b* (as measured between pivot points). In some variations, the first pitch link length may be between about 20% and about 70% of the second pitch link length, or between about 25% and about 65% of the second pitch link length. For example, the first pitch link 1056*a* may rotate relative to the second pitch link 1056*b* without physical interference and allow the pitch assembly 1056 to collapse or fold down against itself into a smaller volume, or more compact configuration. Additionally, a shorter pitch link length may reduce the workspace volume required for the pitch assembly to operate, as a shorter pitch link will sweep a smaller volume throughout its rotation. Such a configuration can, for example, be useful for storage, transport, for reducing risk of collision between the pitch assembly and the patient or surgical personnel, and/or for reducing risk of collision between the pitch assembly and other parts of the robotic arm, etc.

For example, in some variations, the pitch assembly may be part of a four-bar linkage moving as an imperfect parallelogram. For example, as shown in the schematic of FIG. 11A, the distance between pivot points on the first pitch link 1056a may be a distance "A", the distance between pivot points on the second pitch link 1056b may be a distance "B", the distance between a distal pivot point on the second pitch link 1056b and an RCM may be a distance "C", and the distance along a virtual link between the RCM and a proximal pivot point on the first pitch link 1056a may be a distance "D." Distance "A" may be less than distance "C" such that the first link 1056a having effective length "A" and the rotation of the link having effective length "C" are not always parallel as the pitch assembly 1056 and instrument driver 1080 move.

Figure 11B:
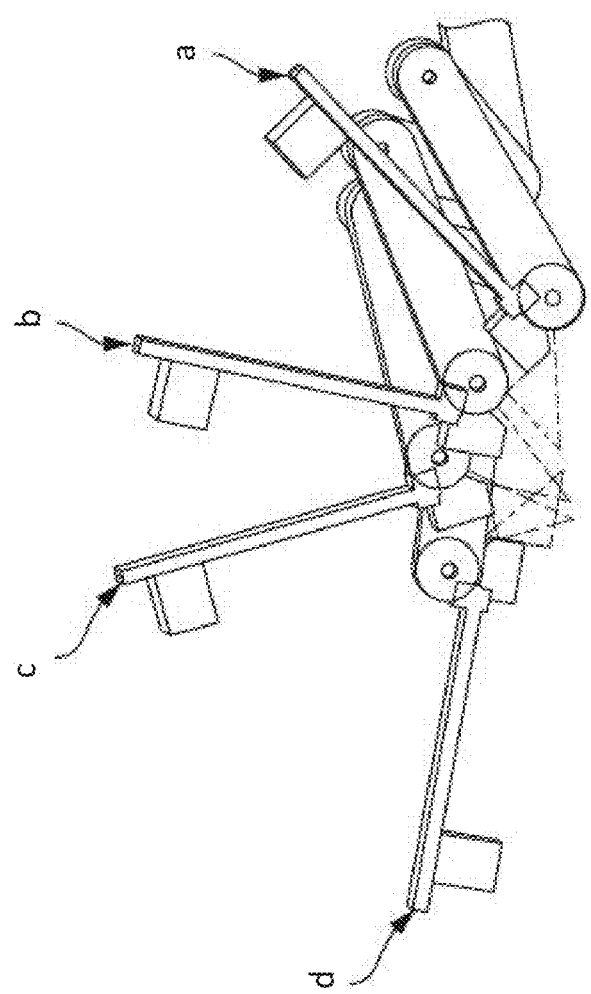
FIG. 11B is a schematic illustration of the spherical pitch assembly depicted in FIG. 11A, moving throughout a series of configurations with a moving remote center of motion.
Figure 11A:
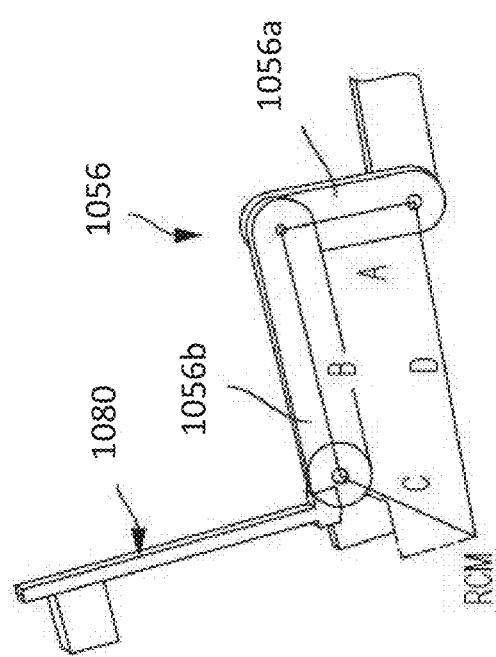
FIG. 11A is a schematic illustration of one exemplary variation of a spherical pitch assembly for a robotic arm.

Furthermore, as pitch assembly 1056 shown in FIG. 11A moves, the RCM tends to move slightly. For example, FIG. 11B illustrates a series of four exemplary poses of the pitch assembly 1056 that are the result of the first pitch link 1056a rotating at its proximal end around Axis G (as noted in FIG. 10D, for example). As the pitch assembly moves through poses "a" through "d" in FIG. 11B, the RCM travels instead of remaining completely stationary, due to the imperfect nature of the parallelogram formed in part by the pitch links. In some variations, movement of the first pitch link 1056a around Axis G may be limited due to the nature of a surgical task being performed. For example, in one exemplary variation, the first pitch link 156a may have a length (as measured between pivot points, described above as distance "A") between about 2 inches and about 4 inches, and the second pitch link 156b may have a length (as measured between pivot points, described above as distance "B") between about 7 inches and about 9 inches. In this exemplary variation, when the arm and instrument driver are performing typical surgical tasks, the pitch range of motion in the seventh joint module 134g may, for example, generally be between about 10 degrees and about 30 degrees. Under such exemplary conditions, the RCM in this exemplary variation may tend to travel between about 1 cm and about 3 cm. It should be understood that in other variations, the first and second pitch links 156a and 156b may have other suitable lengths, and/or the pitch range of motion for surgical tasks being performed may vary, which may cause the RCM to travel less than about 1 cm or more than about 3 cm. In some variations, the first arm segment (e.g., Cartesian arm segment) that is proximal to the pitch assembly may be controlled based on a control algorithm that maintains the RCM point fixed or substantially fixed in space, thereby compensating for the movement of the RCM that would otherwise occur. Such control algorithms or control modes for compensating for a deviating RCM may, for example, be similar to those described herein for maintaining a virtual RCM.

In the exemplary variation shown in FIGS. 12A and 12B, the spherical pitch linkage assembly 1256 includes a series of pulleys and a series of bands connecting the pulleys that facilitate the four-bar linkage movement. First pitch link 1256a is coupled to the output shaft of a joint module actuator that drives rotation of first pitch link 1256a around Axis G, while second pitch link 1256b is rotationally coupled to the instrument driver. First pitch link 1256a includes a first pulley 1210 coupled to the housing of the joint module actuator and located generally at a proximal point of first pitch link 1256a, within an internal space of first pitch link 1256a. First pitch link 1256a also includes a second pulley 1212 located generally at a distal point of first pitch link 1256a, within the internal space of first pitch link 1256a. The second pulley 1212 is rigidly fixed to a proximal point of second pitch link 1256b.

Additionally, second pitch link 1256b includes a third pulley 1214 located generally at a proximal point of second pitch link 1256b, mounted on and rigidly fixed to a shaft of first pitch link 1256a that extends into an internal volume of second pitch link 1256b, such that when first pitch link 1256a rotates, third pulley 1214 rotates correspondingly. Second pitch link 1256b also includes a fourth pulley 1216 located generally at a distal point of second pitch link 1256b, within the internal space of second pitch link 1256b. The instrument driver is rotationally coupled to the distal point of second pitch link 1256b and thus constrained to move when the fourth pulley 1216 rotates.

At least one band (not shown in FIGS. 12A and 12B) wraps around the first and second pulleys such that when a joint module drives rotation of first pitch link 1256a around Axis G, the orientation of the second pitch link 1256b remains fixed relative to the orientation of the housing of the joint module actuator. Similarly, at least one band (not shown) wraps around the third and fourth pulleys such that when the second pitch link 1256b rotates, the instrument driver orientation remains fixed relative to the orientation of the first pitch link 1256a. In sum, rotation of the first pitch link 1256a around Axis G is transformed through the system of pitch links, pulleys, and bands into rotation of the instrument driver around Axis G'. In alternative embodiments, the pulleys may be engaged with cables, belts, and/or other suitable driving members.

The bands connecting the first and second pulleys 1210 and 1212, and the third and fourth pulleys 1214 and 1216, should be appropriately tensioned in order to facilitate the transformation of rotational motion described above. Accordingly, the pitch assembly 1256 may further include a tensioning assembly. For example, the tensioning assembly can include at least one tensioner pulley located in plane with the first and second pulleys 1210 and 1212 and corresponding bands, and at least one tensioner pulley located in plane with the third and fourth pulleys 1214 and 1216 and corresponding bands. The in-plane locations of the tensioning pulleys may be adjusted and set (e.g., with fasteners) in order to calibrate the tension of the bands. However, the pitch assembly 1256 may include a turnbuckle, or any suitable tensioning assembly. The bands may be tensioned to a predetermined tension level during assembly of the pitch assembly, and monitored and re-tensioned during and over the course of use of the robotic arm. Alternatively, at least a portion of the pitch assembly may be swappable to be replaced with appropriately-tensioned pitch assembly parts, such as part of regular maintenance.

Exemplary variations of pulley arrangements (e.g., assemblies for attachment of a driving member to a pulley, tensioning mechanisms, etc.) for the pitch assembly in a robotic arm are further described in detail in U.S. patent application Ser. No. 15/706,582 filed concurrently herewith and titled "BELT TERMINATION AND TENSIONING IN A PULLEY ARRANGEMENT FOR A ROBOTIC ARM", which is hereby incorporated in its entirety by this reference.

The instrument driver 1080 may be configured to orient the surgical instrument within cannula 1090, along instrument Axis H shown in FIG. 10C. The instrument driver 1080 can, for instance, enable rotation of the instrument around Axis H and translation along Axis H, thereby providing two additional DOFs. An alternative way of expressing a two DOF of redundancy may be to include the rotation of the instrument shaft around Axis H (a DOF residing in the instrument driver) with the seven DOF from the first and second arm segments for a total of eight DOF for the robotic arm including the instrument driver, then consider the purpose of the robotic arm to position a vector (the surgical instrument) in space as a six DOF task. Therefore, the eight DOF available to perform such a six DOF task results in two redundant degrees of freedom. The intersection of the spherical roll Axis F, offset pitch Axis G', and the instrument axis H defines the mechanical remote center of motion ("RCM") for the surgical instrument within cannula 190. Generally, the mechanical RCM may closely coincide with the port placement for the surgical instrument (e.g., cannula 1090 couples to the port).

Figure 13:
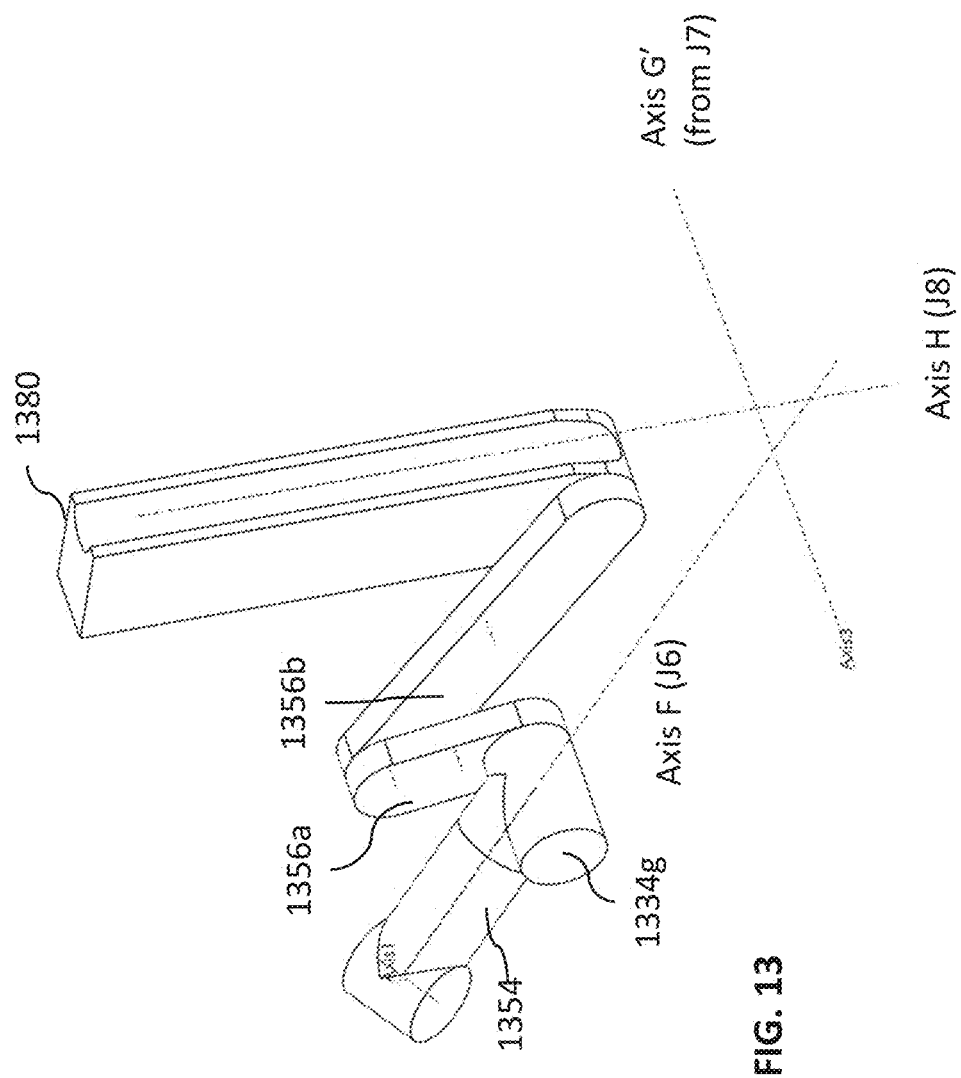
FIG. 13 is a schematic illustration of another variation of a spherical pitch assembly for a robotic arm with offset spherical roll, spherical pitch, and instrument rotation axes.

In some variations, as shown in FIG. 13, at least some of the rotational axes of the second arm segment (spherical arm) do not intersect at a common point. For example, the links in the spherical arm may be configured such that Axis F (a spherical roll axis about which the spherical roll link 1354 rotates), Axis G' (a spherical pitch axis, about which motion is remotely controlled by the joint module 1334*g* with pitch links 1356*a* and 1356*b*), and Axis H (an instrument rotational axis about which the instrument driver 1380 axially rotates the instrument) generally meet in a common region but are offset from one another by a predetermined distance (e.g., between about 1-5 centimeters, or between about 2-4 centimeters, or about 3 centimeters). In some variations, the instrument axis (Axis H) may intersect at an RCM, while the roll axis (Axis F) and/or the pitch axis (Axis G') does not intersect the RCM. For example, the roll axis and/or the pitch axis may be offset by about 5 centimeters or less from the remote center of motion, or about 2 centimeters or less from the remote center of motion. Various lengths of the arm links may be adjusted to accomplish this offset (e.g., shorter first pitch link 1356*a*).

For example, to move the surgical instrument about the same point in 3D space as if that point were a mechanical RCM, a control algorithm for the arm calculates suitable actuation of some or all joints in the arm (including in the first segment, or Cartesian arm) during commanded motions of the instrument, in order to compensate for the axis offsets. For example, in some variations, the offset between a roll axis (Axis F) and an instrument axis (Axis H) may be about 2 centimeters. If the spherical roll link 454 rotates around the roll axis about 90 degrees clockwise as viewed in FIG. 4, the first segment with joints J1-J5 (e.g., Cartesian arm as described above) may collectively move to translate the spherical roll link 454 along an arc with an endpoint about 2 cm up and about 2 cm to the right (as viewed from the perspective of FIG. 4) in order to compensate for the axis offsets and maintain the same effective RCM. Specific rotational movements of each joint J1-J5 may depend on the specific pose of the robotic arm at the time of such motion.

In some areas, the control algorithm for compensating for the offsets may be similar to that implemented in the virtual RCM control mode described in further detail below. Accordingly, a compact arm design may be achieved without sacrificing the ability to maintain desired arcuate range of motion about an effective RCM during teleoperation. One benefit of a robotic arm that embodies these offset spherical roll, spherical pitch, and/or instrument rotation axes is that the robotic arm may be configured to more compactly collapse into a folded configuration. Such a compact configuration may be desirable, for example, for efficient storage under the patient table (or in another suitable storage location, such as in a mobile cart), such that the robotic arm does not impede or otherwise limit the range of motion (e.g., tilting) of the table, nor obstruct imaging fields of view (e.g., medical imaging such as CT scans). Additionally, as described above, in a robotic arm arrangement in which at least one of a spherical roll axis, a spherical pitch axis, and an instrument rotation axis is offset, a reduced workspace volume may be required for the pitch assembly to operate, as a shorter pitch link will sweep a smaller volume throughout its rotation.

In some variations, some or all of the links may include bumpers that may help protect portions of the robotic arm from damage in the event of collision with other links, other joint modules, other robotic arms, surgical assistants or other users, other surgical equipment (e.g., surgical table), and/or other nearby obstacles. The bumpers may additionally or alternatively help protect the robotic arm from damage during packaging and transport. In one embodiment, a bumper may include one or more flexible plates (e.g., thin metal sheets) covering a link, where the plate flexes and absorbs energy upon impact, thereby reducing impact energy transferred to underlying components. In other embodiments, the bumpers may include foam, rubber, inflatable sleeves or other coverings. The bumpers may substantially cover the entire length of the robotic arm, or may cover only selected portions of the robotic arm (e.g., selected links, joint modules). For example, one or more bumpers may cover only part of or the entire length of the spherical segment of the arm, only part of or the entire length of the Cartesian segment of the arm, or a portion of the Cartesian segment and a portion of the spherical segment. As another example, one or more bumpers may cover only some or all of the joint modules in the robotic arm. As yet another example, a bumper may substantially surround a portion of the arm (e.g., circumferentially around the arm) or may cover only part of the circumference of the arm (e.g., a sleeve with an arcuate cross-section). Some or all of the bumpers may be connected to sensors (e.g., pressure sensors, capacitive sensors, etc.) so that the robotic arm can sense occurrence of collisions and/or close approximation to objects in the environment (e.g., other robotic arms, table fixtures, personnel, etc.). Upon detection of a collision or an impending collision, a control system may automatically adjust control of the arm to halt motion in the current direction and/or move in a different direction to reverse or avoid collision.

Generally, each link may include an internal volume for receiving at least one joint module, and/or for passing wiring (e.g., for communication or power) along the length of the robotic arm. For instance, the links may be generally tubular structures. Links may be made of metal (e.g., aluminum, steel, etc.) or other suitable rigid material, and may include parts that are machined, casted, molded, and/or formed through any suitable manufacturing process. Furthermore, a link may include multiple link parts (e.g., shell portions) that are welded or otherwise fastened together to form a generally tubular structure.

Robotic Arm Configurations

The various links in the robotic arm may be arranged in any number of predetermined configurations for different purposes. For instance, a robotic arm (e.g., a variation with offset axes for spherical roll, spherical pitch, and instrument rotation) may be arranged in a compact, folded configuration, such as for stowage under a surgical table, storage, and/or transport. The folded arm configuration may also incorporate the folding, retraction, or other compact storage of components coupled to the robotic arm, such as a table adapter coupling the robotic arm to a surgical patient table, cart, or other surface. FIGS. 14A and 14B illustrate an exemplary folded configuration of a robotic arm in more detail (e.g., a variation without offset axes for spherical roll, spherical pitch, and instrument rotation). Shoulder pitch link 1414 and shoulder roll link 1416 are coaxial to form a shoulder limb 1415, and elbow link 1418 and forearm link 1420 are coaxial to form a forearm limb 1419. In the folded configuration, the shoulder limb 1415 and the forearm limb 1419 may fold toward one another generally arranged in a first plane or "layer." The spherical base link 1452 and spherical roll link 1454 may fold against the forearm limb 1419 such that the pitch assembly (pitch links 1456a and 1456b) is generally arranged in a second plane or "layer." The instrument driver 1480 may be tucked between the first and second "layers."

Figure 15A:
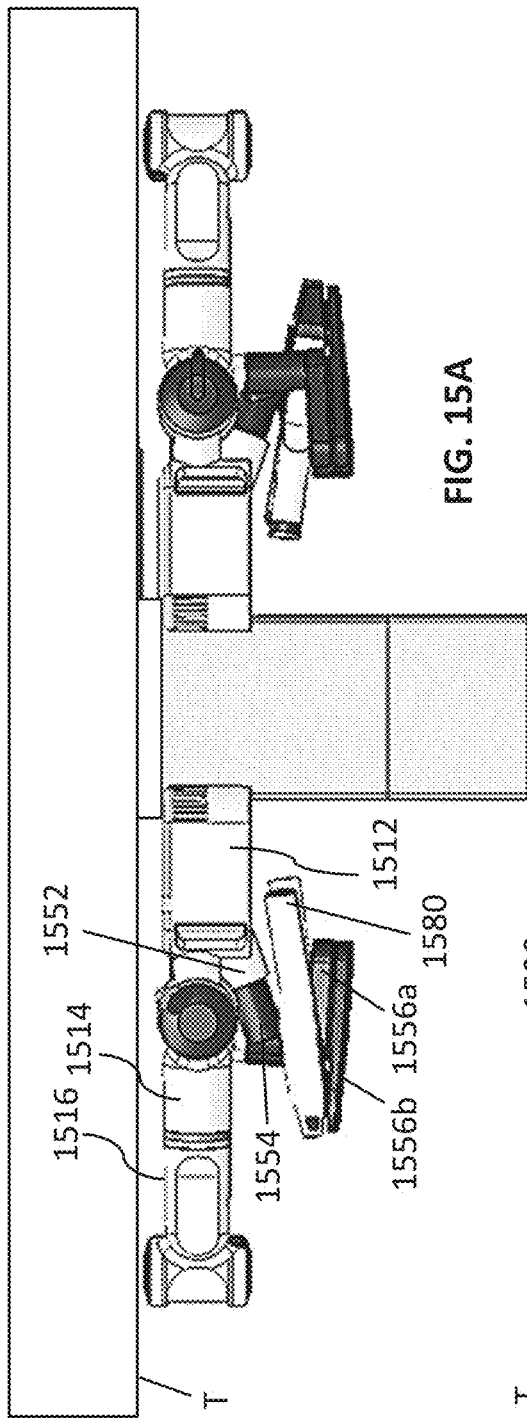
FIGS. 15A and 15B are side and bottom views of a robotic surgical system including a plurality of robotic arms in a folded configuration and coupled to a patient table.
Figure 15B:
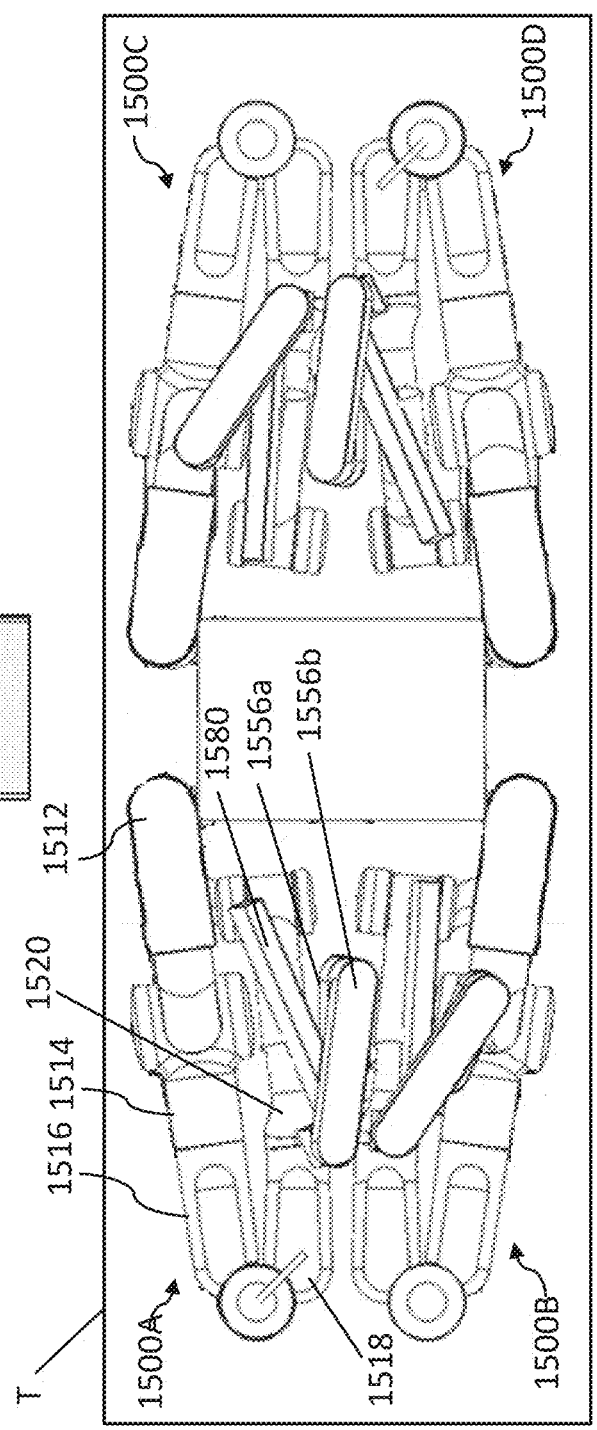

FIGS. 15A and 15B illustrate exemplary variations of robotic arms arranged in an exemplary folded configuration underneath a surgical patient table. This exemplary folded configuration may be used, for example, for storage and/or transport purposes. Referring to robotic arm 1500A in FIG. 15B, in some variations, a robotic arm may include a base link 1512 configured to couple to a table T, such as with pins or other suitable adapter. The base link 1512 may, for example, couple to a column support of the table T that grounds the table T to the floor. The robotic arm may include a shoulder pitch link 1514 coupled to the base link 1512, and a shoulder roll link 1516 coaxial with and coupled to the shoulder pitch link 1514. An elbow link 1518 is pivotally coupled to the shoulder pitch link 1514 such that a forearm portion of the robotic arm (including elbow link 1518 and forearm link 1520) is foldable against the shoulder portion (including shoulder pitch link 1514 and shoulder roll link 1516) of the robotic arm. For example, the forearm portion of the robotic arm may be generally doubled-back on the shoulder portion of the robotic arm, with the shoulder portion and the forearm portion of the robotic arm generally located in the same plane or "layer." As best shown in FIG. 15A, the spherical base link 1552 (which is coupled to the forearm link 1520) may be oriented at an angle out of plane from the shoulder portion and the forearm portion. At least the rest of the spherical arm segment of the robotic arm, including the spherical roll link 1554 (which is coupled to the spherical base link 1552), the first pitch link 1556a, and the second pitch link 1556b, may arranged out of plane from the shoulder portion and the forearm portion of the robotic arm. For example, at least a proximal portion of the spherical roll link 1554 may be coaxial with the spherical base link 1552 to continue out of plane from the more proximal portions of the robotic arm. The first and second pitch links 1556a and 1556b may be arranged below the plane of the shoulder and forearm portions of the robotic arm. The instrument driver 1580 may be tucked or collapsed between the spherical roll link and at least one of the first and second pitch links 1556a and 1556b. In some variations, for example, the stowage configuration of an arm shown in FIGS. 15A and 15B may occupy a volume of generally between about 8 and about 12 inches high (along the vertical height of the table), between about 8 and about 12 inches wide (along the width of the table), and between about 18 and 22 inches long (along the longitudinal length of the table). In one exemplary variations, for example, the stowage configuration of an arm may occupy a volume of about 10 inches high, about 10 inches wide, and about 20 inches long.

Although FIG. 15B depicts four robotic arms 1500A, 1500B, 1500C, and 1500D arranged in a 2×2 arrangement (i.e., so each robotic arm services or is coupled to a respective quadrant of the table T), it should be understood that a robotic surgical system may include fewer (e.g., one, two, or three) or more (four, five, six, etc.) robotic arms arranged in any suitable manner. Furthermore, in some variations one or more of the robotic arms may be permanently coupled to the table, while in other variations one or more of the robotic arms may be removably coupled to the table. For example, at least part of the system may be modular, with one or more of the robotic arms selectively removable and/or rearrangeable). Exemplary variations of coupling mechanisms to couple a robotic arm to a patient table are described in further detail in U.S. patent application Ser. No. 15/706,112 filed concurrently herewith and titled "LINKAGE MECHANISMS FOR MOUNTING ROBOTIC ARMS TO A SURGICAL TABLE", and U.S. patent application Ser. No. 15/706,087 filed concurrently herewith and titled "TABLE ADAPTERS FOR MOUNTING ROBOTIC ARMS TO A SURGICAL TABLE", each of which is incorporated in its entirety by this reference.

Robotic Arm Control System

The signals from one or more multi-DOF sensors may be used as inputs for a control system for a robotic system. For example, a robotic-assisted surgical system may include a control system that governs actions of the robotic arm (or multiple robotic arms, if the robotic-assisted surgical system includes more than one robotic arm). As shown in FIG. 17, the control system may include one or more processors 1750 (e.g., a microprocessor, microcontroller, application-specific integrated circuit, field programmable gate array, and/or other logic circuitry). The processor 1750, which may be physically located on the robotic arm itself, in a cart-carried unit, or other suitable structure, may be communicatively linked to a console (e.g., user interface). The control system may further include a set of multiple motor controllers (e.g., 1754a, 1756a, 1758a, 1760a, 1762a, 1764a, and 1766a), each of which is communicatively coupled to the processor 1750 and dedicated to control and operate at least one actuator in a respective joint module in the robotic arm (e.g., 1754b, 1756b, 1758b, 1760b, 1762b, 1764b, and 1766b).

Figure 18:
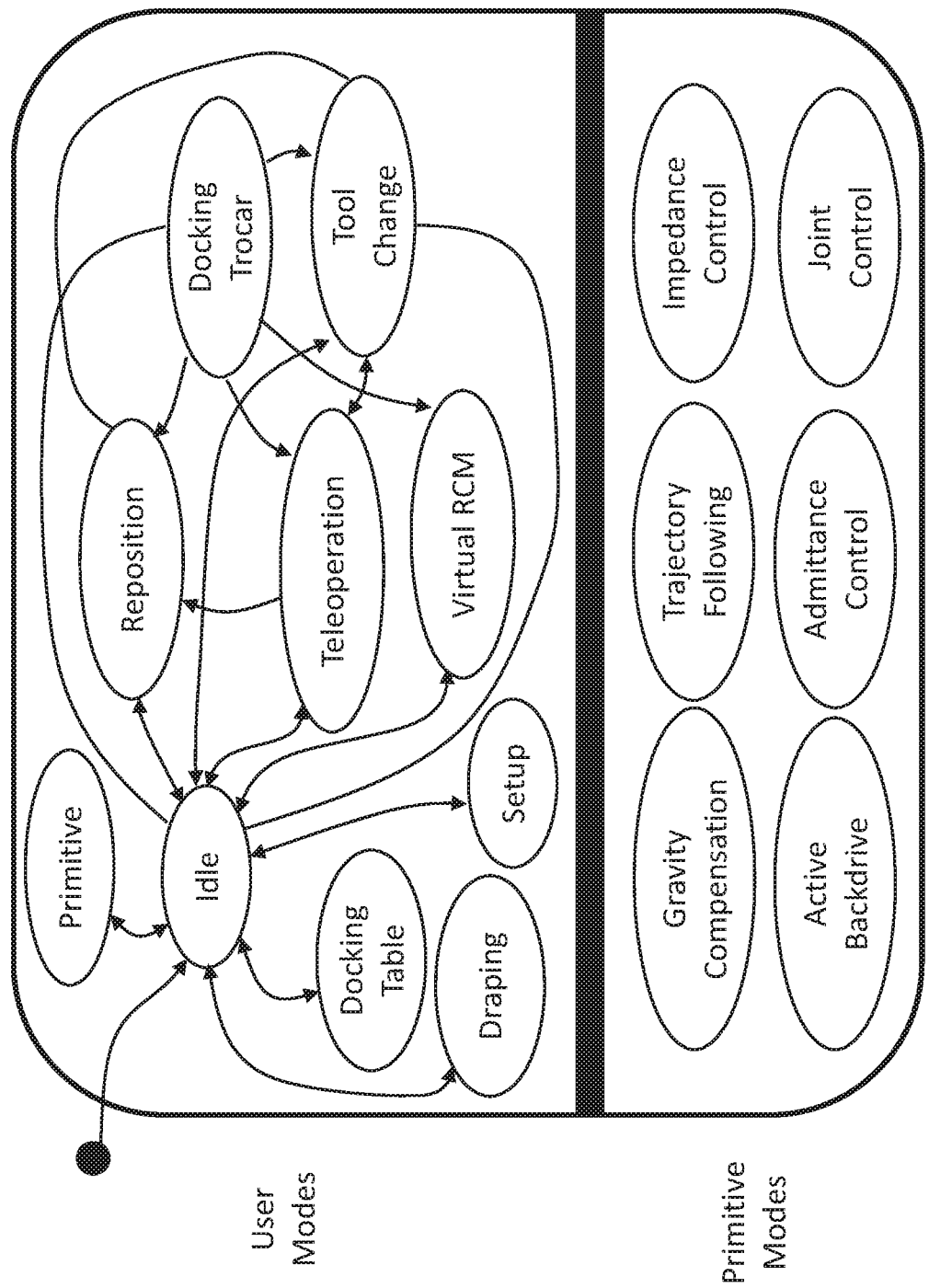
FIG. 18 is a state diagram summarizing primitive modes and user modes for one variation of a control system for a robotic arm.

As shown in FIG. 18, the control system may be configured to actuate at least one joint module based on one or more control modes. For example, a control mode may be classified as a primitive mode (which governs the underlying behavior for actuation of at least one joint module) or as a user mode (which governs higher level, task-specific behavior and may utilize one or more primitive modes). In some variations, a user may select a particular control mode through a user interface device (e.g., selecting a particular mode from an operation command list) or by activating buttons, touchscreens, or other touchpoint surface such as those described above on the surface of the robotic arm. Upon a user engaging a particular touchpoint surface, the switching between the various control modes may, for example, be handled by a state machine/controller. Exemplary primitive modes and user modes of a control system, at least some of which may implement force and/or torque measurements received from a force/torque sensor (e.g., a multi-DOF capacitive sensor described herein), are described below.

In some variations, a primitive mode may be the smallest functional block that enables the robotic arm to carry out a particular task (e.g., actuate a joint module to increase or decrease the angle between arm links on either side of the joint module). As shown in FIG. 18, one example of a primitive control mode is a joint command mode, which allows a user to directly control a single joint module actuator individually, and/or multiple joint module actuators collectively. In the joint command mode, the robotic arm may be commanded joint-by-joint. The commands are direct or "pass through," in that outputs are the same as inputs. For instance, the inputs/outputs of the control system include joint module indices (e.g., index defining which joint module is associated with the command), an indication of the commanded mode (defining whether commands are to control the current or power to the one or more actuators in the joint module, the rotational position of the one or more actuators in the joint module, the rotational velocity of the one or more actuators in the joint module, etc.), and an indication of the reference command (values for the commanded current, position, velocity, etc.). In some variations, the joint command mode may include some error handling steps on the joint module and/or actuator level. For instance, the joint command mode may include a check that the joint command will not cause the joint module to exceed its physical limit, and/or a check that the joint command will not exceed the current limits of the one or more actuators. In some variations, the joint command mode may, for example, be used for system tuning and testing.

As shown in FIG. 18, another example of a primitive control mode is gravity compensation mode, in which the robotic arm holds itself in a particular pose (i.e., particular position and orientation of the links and joint modules) without drifting downward due to gravity. In gravity compensation mode, the control system determines the gravitational force acting on at least a portion of the links in the robotic arm. In response, the control system actuates at least one joint module to counteract the determined gravitational force such that the robotic arm can maintain the current pose. To determine the gravitational force, the controller may perform calculations based on measured joint angles between adjacent links, known kinematic and/or dynamic properties of the robotic arm and instrument driver, and/or known characteristics of the actuator (e.g., gear ratio, motor torque constants), etc. Furthermore, the robotic arm may include at least one accelerometer or other suitable sensor configured to determine the direction of the applied gravitational force on the arm. Based on these calculations, the controller may algorithmically determine what force at each joint module is needed to compensate for gravitational force acting on that joint module. For instance, the controller may utilize a forward kinematic algorithm, an inverse dynamic algorithm, or any suitable algorithm. The controller may then generate a set of commands to provide the actuators in the joint modules with appropriate level of current which holds the robotic arm in the same pose. The gravity compensation mode may, for example, be used alone or in combination with other modes in user modes described below, such as docking mode, draping mode, setup mode, and/or instrument change mode (e.g., coupling a surgical instrument to the instrument holder, swapping an existing surgical instrument in the instrument holder with a new surgical instrument, etc.).

As shown in FIG. 18, another example of a primitive control mode is friction compensation mode, or active back-drive mode. Often, a user may want to directly manipulate (e.g., pull or push) one or more of the arm links to arrange the robotic arm in a particular pose. These actions back-drive the actuators of the robotic arm. However, due to friction caused by mechanical aspects such as high gear ratios in the joint modules, the user must apply a significant amount of force in order to overcome the friction and successfully move the robotic arm. To address this, the friction compensation mode enables the robotic arm to assist a user in moving at least a portion of the robotic arm, by actively back-driving appropriate joint modules in the direction needed to achieve the pose desired by the user. As a result, the user may manually manipulate the robotic arm with less perceived friction or with an apparent "lightweight" feel. In some variations, the controller may also incorporate pre-defined parameters (e.g., duration of a force) to help distinguish between movement that is accidental (e.g., a brief bump of an arm) and a sudden intended shift in arm position, then correct or reestablish arm position in the event a movement is determined to be accidental. In friction compensation mode, the control system determines the presence and direction of a user-applied force acting on at least one joint module (either directly or indirectly as the result of force on one or more arm links) to back-drive the actuator in that joint module. In response, the control system actuates the joint module in the same direction as the user-applied force to help the user overcome static or dynamic friction. To determine the presence, magnitude, and direction of the user-applied force, the control system may monitor the velocity and/or position of the joint modules or robotic links (e.g., with force or torque sensors, accelerometers, etc.). Additionally, when in friction compensation mode, the control system may send a dithering current signal to (e.g., a sine wave or square wave centered at zero, with frequency of about 0.5 Hz -1.0 Hz or other suitable frequency, and with amplitude within the friction band in both directions) one or more joint modules, such that the joint modules are primed to nearly, but not quite, overcome friction in either actuator direction. In response to determining the presence and direction of user-applied force, the control system may then generate a set of commands to provide the actuators in the joint modules with appropriate level of current to more responsively overcome friction. The friction compensation mode may, for example, be used alone or in combination with other modes during docking, instrument change, etc.

As shown in FIG. 18, another example of a primitive control mode is trajectory following mode, in which the robotic arm may move to follow a sequence of one or more Cartesian trajectory commands. Trajectory commands may include, for example, velocity commands (framed in terms of linear and/or angular movement) or target pose commands (framed in terms of end objective position and orientation of the links and joint modules, such as a template pose for a particular kind of surgical procedure). If the command is a target pose that requires a number of link movements to transition from a current pose to the target pose, then the control system may generate a trajectory (defining the necessary link movements). If the command relates to a target pose that is the same as the current pose, then the control system may generate trajectory commands effectively resulting in a commanded "hold" position. For instance, the trajectory may be based on inputs including: commanded velocities or poses (e.g., transformation matrix, rotation matrix, 3D vector, 6D vector, etc.), the arm links to be controlled, measured joint parameters (angles, velocities, accelerations, etc.), tool parameters (type, weight, size, etc.), and environmental parameters (e.g., predefined regions which the arm link is barred or forbidden from entering, etc.). The control system may then use one or more algorithms to generate the outputs of commanded joint parameters (position, velocity, acceleration, etc.) to the firmware and/or commanded motor currents as current feedforward to the firmware. Suitable algorithms for determining these output commands include algorithms based on forward kinematics, inverse kinematics, inverse dynamics, and/or collision avoidance (e.g., collision between arm links, between different instances of the robotic arm, between the arm and environment, etc.). The trajectory following mode may, for example, be used alone or in combination with other modes in user modes described below, such as docking table mode, a draping mode, a setup mode and/or instrument change mode.

As shown in FIG. 18, another example of a primitive control mode is an impedance control mode, which allows the robotic arm to be compliant to a virtual environment without using a force and/or torque sensor. Generally, impedance control modulates the mechanical impedance of a mechanical system. Mechanical impedance of a system is defined as the ratio of force output of the system to motion input to the system. By controlling the mechanical impedance of the system, one may control the amount of the system's resistance to environment-imposed external motions. For instance, the impedance control mode may use a spring and damper system to model the surrounding environment, where a spring constant defines the force output for a modeled spring, and a damping constant defines the force output for a given velocity input. In some variations, one application of the impedance control mode is the creation and use of a virtual fixture, or haptics, such that the robotic arm can complete an operation (i.e., movement) that is compliant with defined restrictions, such as the environment and/or one or more virtual, geometric constraints applied to the robotic arm. One exemplary type of a virtual fixture is a "forbidden region" virtual fixture, which prevents the arm from entering into a predefined space in the environment (e.g., for collision avoidance). Another exemplary type of a virtual fixture is a "guidance" virtual fixture, which provides a guided motion to the arm by geometrically constraining range of motion limits of the arm (e.g., constraining relative motion of arm links). Control techniques in the impedance control mode can be framed as controlling the joint space (controlling actuation of each joint module) and/or Cartesian space (controlling the arm location in space). Inputs to the control algorithm may include measured joint angles and/or velocities of one or more portions of the robotic arm, selected virtual fixture configuration, and location of a targeted control point on the robotic arm. The control system may then use one or more algorithms to generate commanded joint actuator parameters (required current/torque, etc.) and/or status of the compliance to the imposed constraints. Suitable algorithms for determining these output commands include algorithms based on forward kinematics, inverse kinematics, inverse dynamics, collision avoidance (e.g., collision between arm links, between different instances of the robotic arm, between the arm and environment, etc.), and/or virtual force rendering (with the use of a virtual model such as geometric shape, mass, spring-and-damper, etc.). The impedance control mode may, for example, be used alone or in combination with other modes during instrument change.

As shown in FIG. 18, another example of a primitive control mode is an admittance control mode, which allows the robot arm to respond to sensed user force according to a virtual model (e.g., virtual mass/inertia properties). For instance, in response to one or more force/torque sensors that measure user force directed on the robotic arm, the actual robotic arm may move in the same manner that the virtual arm model would if the user pushed/pulled on the virtual arm model in the same manner. In some variations, the user force is measured at least with torque sensors in one or more joint modules in the arm. In other variations, the user force is measured at least with a six DOF force/torque sensor on one or more links of the robotic arm (e.g., such as the six DOF capacitive sensor described above) or multiple sensors detecting up to six DOF in aggregate (e.g., two 3 DOF sensors). The control system may take as an input the actual force/torque sensor readings, the force/torque sensor transformations to map the actual robotic arm to the virtual model, the virtual model transformations to map parameters to a known reference frame of the robotic arm, other virtual model properties, and/or robotic arm and instrument driver kinematics. The control system may then use one or more algorithms to generate commands to joint module actuators for particular current, torque, joint positions, and/or other suitable joint module parameters, in order to cause the robotic arm to move according to the virtual mode. Suitable algorithms for determining these output commands include algorithms based on forward kinematics, inverse kinematics, inverse dynamics, collision avoidance, and/or forward dynamics for the virtual model. The admittance control mode may, for example, be used alone or in combination with other modes during port docking or instrument change.

In some variations, user modes may be control modes that overlay on top of primitive modes, in that a user mode can incorporate one or more primitive modes described above. The user modes allow the user to physically interact with the robotic arm in a number of different ways during different phases of a surgical procedure (e.g., during pre-operation setup and testing, surgery, post-operation tear-down and storage). For instance, certain user modes allow the robotic arm to react in a certain way depending on a particular combination of incorporated primitive modes. Additionally, certain user modes may involve a predetermined sequence of automated movement steps designed to increase efficiency for a particular phase of the surgical procedure. Many user modes are mutually exclusive from one another and cannot be selected simultaneously, but some user modes (e.g., teleoperation mode and virtual RCM mode) may operate in parallel.

As shown in FIG. 18, one example of a user mode is an idling mode, in which the robotic arm may rest in a current arm pose or a default arm pose awaiting further commands or instruction. In one variation, the idling mode incorporates the trajectory following mode described above, defining the target pose as the same as the current pose, thereby resulting in a commanded "hold" position. In another variation, the idling mode additionally or alternatively incorporates the gravity compensation mode described above.

As shown in FIG. 18, another example of a user mode is a setup mode, in which a robotic arm may transition from a first pose (e.g., folded configuration for storage and transport) to a default pose (e.g., at least partially extended) such as a default setup pose or a predetermined template pose for a particular type of surgical procedure. Additionally, the robotic arm may initialize itself by completing a predetermined checklist (e.g., safety and functionality checks) of action items. The movement to a default pose and/or the checklist completion may be at least partially automatic or autonomous. Readiness of the robotic arm for use may be confirmed by a user and/or supervisory control system. While the robotic arm is in the setup mode, users may perform various pre-operative tasks on the robotic arm, such as inspection (e.g., visually or manually), cleaning, draping, etc.

As shown in FIG. 18, another example of a user mode is a mounting mode, in which the robotic arm is connected to an operative platform (e.g., surgical table or cart) and/or initialized for setup. For instance, while being connected to the operative platform, the robotic arm may rest in a current arm pose (e.g., the default pose achieved at the end of the action sequence in the setup mode). Similar to the idling mode, the docking table mode may incorporate the trajectory following mode resulting in a commanded "hold position", and/or may incorporate the gravity compensation mode described above.

As shown in FIG. 18, another example of a user mode is a draping mode, in which the robotic arm facilitates the process in which sterile barriers are coupled to the robotic arm (to maintain a sterile barrier between the robotic arm and the surgical instrument). For example, in the draping mode, the robotic arm may automatically move itself to a pre-determined draping pose, such as extended away from the patient and closer to a surgical assistant, that improves access to regions requiring the attachment of sterile barriers (e.g., at the instrument attachment point on the instrument driver). The surgical assistant may, for instance, walk around the patient table to each of multiple robotic arms in the draping poses to sequentially attach the sterile barrier to each individual robotic arm. Alternatively, the multiple robotic arms may automatically move closer to the surgical assistant so that the surgical assistant may remain stationary, thereby improving setup efficiency. For instance, when the sterile draping on a first robotic arm is complete and a second robotic arm is ready to be similarly draped, the control system may move the first robotic arm away to another position and may move the second robotic arm closer to the surgical assistant (e.g., after using sensors to automatically detect sterile barrier attachment, and/or after a user command indicating that the draping is complete). Furthermore, during draping, the user may be able to adjust the shape and position of the robotic arm to adapt to specific circumstances, such as clutter in the room, size of the patient, and/or limited height of the surgical assistant performing draping. In some variations, the draping mode may incorporate the joint command mode and/or gravity compensation mode to control the robotic arm.

As shown in FIG. 18, another example of a user mode is a docking mode, in which the robotic arm facilitates the process in which the user attaches the robotic arm to a port (with cannula pre-inserted into the patient's body) on the patient. In order to perform minimally-invasive surgery, the distal end of the robotic arm is generally rigidly latched to the port using gross or coarse positioning and fine positioning steps. During gross positioning, the surgical assistant may manually guide the distal end of the robotic arm closer to the port (e.g., within about six inches, or other suitable distance to the port) by grabbing, pushing, pulling, or otherwise manually the arm directly (alternatively while grasping a handle, or by manipulating a joystick, D-pad, or other user interface touchpoint). During gross positioning, gravity compensation and/or friction compensation may be applied at the arm joints as described above. Furthermore, in some variations, in order to prevent accidental or inadvertent bumps from moving the arm undesirably, the user's manually applied force may be required to overcome a threshold virtual spring force before the user's force causes the arm to move. During fine positioning, the surgical assistant may further manually guide the distal end of the robotic arm to couple to the cannula inserted in the port. Fine positioning may be further enabled with the use of a fine positioning clutch 170 (e.g., located on the spherical arm 150, near the instrument driver as shown in FIG. 1D and described above), such as a trigger, button, switch, etc. Upon engagement of the fine positioning clutch 170, the linkages of the first arm segment (Cartesian arm segment) may move under user guidance similar to during gross positioning, while locking at least some of the joint modules of the linkages of the second arm segment (spherical arm segment) such that at least some of the linkages of the second arm segment do not move relative to one another. During these steps, the control system may operate the robotic arm in gravity compensation mode and/or friction compensation mode described above.

As shown in FIG. 18, another example of a user mode is a teleoperation mode, in which the robotic arm is remotely controlled by a user interface device during the surgical procedure. While in the teleoperation mode, typically the Cartesian arm segment may be fixed in space (thereby preserving the mechanical RCM and the corresponding range of motion of the end effector) and the motion of the end effector may be controlled by the spherical arm segment and the instrument driver. The teleoperation mode may incorporate the gravity compensation mode, the trajectory following mode, and/or impedance control mode described above. In some variations, the trajectory following mode and/or the impedance control mode may focus on collision avoidance (e.g., with other robotic arms) while the robotic arm is in teleoperation mode.

As shown in FIG. 18, another example of a user mode is a repositioning mode, in which the user may move the robotic arm in a new pose without changing the end effector instrument position and orientation. This kind of repositioning is possible due to the redundant DOFs in the robotic arm. For instance, the distal end of the robotic arm may remain docked to the port (allowing the mechanical RCM and the instrument to remain fixed in space) while the robotic arm is moved around the instrument driver. In the repositioning mode, the control system knows where the instrument is located, and tracks arm movement as the user repositions the robotic arm so as to avoid collisions with the robotic arm. Alternatively, the robotic arm may disengage from the instrument while the instrument is still inserted in the patient, then the robotic arm may reposition and subsequently reengage the instrument. After the robotic arm settles into a new pose and reengages with the instrument, the control system may initiate a check to help ensure that the functionality and control of the instrument is behaving correctly. The repositioning mode may incorporate the gravity compensation mode, trajectory following mode, and/or impedance control mode described above.

As an illustrative example, when the robotic arm is in the repositioning mode, the entire robotic arm may operate with gravity compensation. At least part of the first segment of the robotic arm (e.g., at least a portion of the Cartesian arm segment) may be passive, with joint modules that are passively back-drivable. At least part of the second segment of the robotic arm (e.g., at least a portion of the spherical arm segment) may be active, with joint modules that are locked in an active "hold" position in trajectory following mode in order to maintain the RCM and end effector position/orientation. After the robotic arm receives a user force (e.g., push or pull) on the robotic arm, the user force is propagated to the passive joint modules and causes the passive joints to move generally in compliance with the user force, with some constraints (e.g., implemented through impedance control). In particular, certain features (e.g., the distal most end of the passive arm segment) may be constrained on the surface of a virtual fixture, such as a generally spherical surface, such that the passive arm segment can only move within the regions not forbidden by the virtual fixture. While the passive arm segment is moving, the joint modules in the active arm segment may be actively driven to maintain a substantially constant/stable instrument and RCM position and angle, despite the passive arm segment being pushed to a new location on the virtual spherical surface. As shown in FIG. 19, another example of a user mode is virtual RCM mode, in which the robotic arm establishes a virtual remote center of motion that is not coincident with the mechanical remote center of motion. The virtual remote center of motion is created as the result of software combined with mechanical design. Typically, during a surgical procedure, the mechanical RCM is preserved by fixing the pose of the Cartesian arm segment and moving the spherical arm segment (i.e., during teleoperation mode). However, in the virtual RCM mode, the mechanical RCM can move in order to create better physical clearance between the robotic arm and the patient, while maintaining the previous effective range of motion of the end effector at a virtual RCM. The virtual RCM is achieved by moving both the Cartesian arm segment and spherical arm segment, as the Cartesian arm segment creates the offset between the mechanical and virtual RCMs. In contrast to the mechanical RCM, the virtual RCM can dynamically change, such as during a surgical procedure or between different surgical procedures. In some variations, the virtual RCM mode may incorporate the gravity compensation mode and trajectory following mode, or alternatively may incorporate the gravity compensation mode and the impedance control mode.

In some instances, the virtual RCM may be compliant, in that rather than being constrained to a point, the virtual RCM may be constrained to a plane which is generally normal to the instrument shaft axis and intersects the instrument shaft axis at a specified height relative to the mechanical RCM. In such instances, the joints of the Cartesian arm operate in gravity compensation, active back drive, and/or impedance control modes such that the joints allow the arm to respond to forces in line with the virtual plane, but resist forces perpendicular to the plane. The joints of the spherical arm (e.g., J6 and J7) and the joints of the instrument driver are still in trajectory following mode, thereby allowing the user to optionally continue driving the instrument and performing surgery. This allows the robotic arm to naturally find the pivot point which creates a low amount of force on the patient's tissue, while preventing the instrument and cannula from being pulled or pushed into or out of the patient. Such a mode of operation may be useful, for example, during cases with large instrument ranges of motion (e.g., multi-quadrant procedures) in which only a single, fixed pivot point may not be ideal. Other cases, such as procedures for operating on overweight/obese patients with thicker tissue layers, and thoracic procedures in which the cannula and instrument pass between ribs, may also benefit from such a compliant virtual RCM mode. The compliant virtual RCM mode may be used in conjunction with teleoperation mode or it may be engaged by the user selectively and intermittently. This mode may also be useful during cases in which the patient table is tilted during the procedure, as it would allow the arm to compliantly follow any shifts in patient tissue that result from the shift of the table (e.g., from Trendelenburg to reverse Trendelenburg position).

As shown in FIG. 18, another example of a user mode is instrument change or instrument change mode, in which multiple joint modules of the robotic arm may act to move the surgical instrument in or out of the cannula (e.g. translation along instrument axis H) beyond the range of motion available by actuating solely the distalmost joint module. By moving the surgical instrument further out of the cannula (for instance, with an actuated cannula latch mechanism, e.g. operated by a motor, so that the cannula may be detached without a user's manual direct assistance), the robotic arms may easily dock or change between cannulae and instruments. In some variations, the instrument change mode may additionally or alternatively allow automatic instrument change in which the control system commands automatically taking the instrument out of the cannula, changing end effector tips or instruments, and re-docking the robotic arm to the cannula. Various selected end effector tips may be arranged in a pre-defined order on a surface (e.g., table), such that the control system may locate and identify desired end-effector tips for an automatic instrument change operation. In some variations, the instrument change mode may incorporate gravity compensation mode and trajectory following mode.

Other user modes may be programmed into the control system that incorporate and combine aspects of the various control modes described above. For example, another example of a user mode is a post-operative mode which may be similar to the set-up mode, except some steps may occur in a different order (e.g., system check, followed by folding the robotic arm into a folded configuration for storage). The post-operative mode may also include triggering a complete power off cycle. Other potential modes include a servicing mode, cleaning mode (e.g., move the robotic arm into a fully extended pose to increase exposed surface area during cleaning or sterilization), inspection mode, parade or marketing mode (e.g., pre-programmed series of movements for demonstration poses), cycle testing mode, and/or any other suitable mode.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A capacitive sensor for characterizing at least one of force and torque, comprising:
   a first plurality of non-patterned conductive regions and a first plurality of patterned conductive regions disposed on a first surface of a first plate; and
   a second plurality of non-patterned conductive regions and a second plurality of patterned conductive regions disposed on a second surface of a second plate;
   wherein the first and second pluralities of non-patterned conductive regions are facing each other and the first and second pluralities of patterned conductive regions are facing each other when the first surface of the first plate is facing the second surface of the second plate.

2. The capacitive sensor of claim 1, wherein the capacitive sensor measures at least one of relative lateral translation and relative rotation between the first and second surfaces based at least partially on area of overlap between the first and second pluralities of patterned conductive regions.

3. The capacitive sensor of claim 1, wherein the capacitive sensor measures relative axial displacement between the first and second surfaces based at least partially on gap distance between at least one of the first plurality of non-patterned conductive regions and at least one of the second plurality of non-patterned conductive regions.

4. The capacitive sensor of claim 1, wherein the second surface is spaced apart from and generally axially aligned with the first surface.

5. The capacitive sensor of claim 1, wherein at least one of the first plurality of patterned conductive regions comprises at least a first group of conductive strips and a second group of conductive strips.

6. The capacitive sensor of claim 5, wherein the first group of conductive strips and the second group of conductive strips are arranged in an alternating pattern on the first surface.

7. The capacitive sensor of claim 5, wherein at least one of the second plurality of patterned conductive regions comprises a third group of conductive strips, wherein one of the third group of conductive strips faces a portion of the first group of conductive strips and a portion of the second group of conductive strips.

8. The capacitive sensor of claim 1, further comprising at least two reference conductive pads disposed on the first surface.

9. The capacitive sensor of claim 1, further comprising at least one reference conductive pad disposed on at least one of the first and second plates.

10. The capacitive sensor of claim 1, wherein the second plurality of non-patterned conductive regions and the second plurality of patterned conductive regions are conductively coupled as a common ground.

11. The capacitive sensor of claim 1, wherein the first plurality of patterned conductive regions are arranged around a center point.

12. The capacitive sensor of claim 11, wherein the first plurality of patterned conductive regions are arranged equally distributed from one another around the center point.

13. The capacitive sensor of claim 12, wherein the first plurality of patterned conductive regions comprise three patterned conductive regions arranged approximately 120 degrees from one another.

14. The capacitive sensor of claim 1, further comprising a base, wherein the first plurality of non-patterned conductive regions and the first plurality of patterned conductive regions are fixed relative to a first base portion of the base, and wherein the second plurality of non-patterned conductive regions and the second plurality of patterned conductive regions are fixed relative to a second base portion of the base.

15. The capacitive sensor of claim 14, wherein at least part of the first base portion and at least part of the second base portion are rotationally displaceable relative to each other.

16. The capacitive sensor of claim 14, wherein at least part of the first base portion and at least part of the second base portion are laterally displaceable relative to each other.

17. The capacitive sensor of claim 14, wherein at least part of the first base portion and at least part of the second base portion are axially displaceable relative to each other.

18. The capacitive sensor of claim 14, further comprising a cover configured to couple to the base such that the cover and the base enclose the first and second surfaces.

* * * * *